(12) United States Patent
Wilner et al.

(10) Patent No.: US 11,454,624 B2
(45) Date of Patent: Sep. 27, 2022

(54) NANOPORE TECHNOLOGIES

(71) Applicant: SENSONANO LTD., Tel Aviv (IL)

(72) Inventors: Ofer Israel Wilner, Ramat HaSharon (IL); Ori Kaplan, Tel Aviv (IL)

(73) Assignees: Ofer Wilner, Ramat Hasharon (IL); Ori Kaplan, Lachish (IL)

( * ) Notice: Subject to any disclaimer, the term of this patent is extended or adjusted under 35 U.S.C. 154(b) by 546 days.

(21) Appl. No.: 16/584,205

(22) Filed: Sep. 26, 2019

(65) Prior Publication Data
US 2020/0103392 A1 Apr. 2, 2020

(30) Foreign Application Priority Data

Sep. 28, 2018 (GB) .................................. 1815931

(51) Int. Cl.
*G01N 33/487* (2006.01)
*G01N 27/26* (2006.01)
*B82Y 5/00* (2011.01)

(52) U.S. Cl.
CPC ....... *G01N 33/48721* (2013.01); *G01N 27/26* (2013.01); *B82Y 5/00* (2013.01)

(58) Field of Classification Search
None
See application file for complete search history.

(56) References Cited

U.S. PATENT DOCUMENTS

| 2014/0262820 | A1 | 9/2014 | Kuan et al. |
| 2015/0109008 | A1 | 4/2015 | Godin et al. |
| 2016/0327513 | A1 | 11/2016 | Yanagi et al. |
| 2017/0327880 | A1 | 11/2017 | Jones |
| 2017/0363609 | A1 | 12/2017 | Tabard-cossa et al. |

(Continued)

FOREIGN PATENT DOCUMENTS

| WO | 2013/167955 | 11/2013 |
| WO | 2014/144818 | 9/2014 |

(Continued)

OTHER PUBLICATIONS

Yanagi, Itaru, et al. "Fabricating nanopores with diameters of sub-1 nm to 3 nm using multilevel pulse-voltage injection." Scientific reports 4 (2014): 5000.

(Continued)

*Primary Examiner* — J. Christopher Ball
(74) *Attorney, Agent, or Firm* — Sughrue Mion, PLLC

(57) ABSTRACT

A test cartridge includes a membrane separating an internal space of the cartridge into a sample chamber and a second chamber. A first electrode is disposed within the sample chamber, and a second electrode is disposed within the second chamber. A device includes a dock and circuitry. The dock includes a first dock-terminal and a second dock-terminal, and is configured to receive the cartridge such that the circuitry is electrically connected to the electrodes via contact between terminals of the dock and terminals of the cartridge. The circuitry performs, while the cartridge remains docked with the dock: (a) a verification step that verifies an absence of nanopores in the membrane, (b) subsequently, a nanoporation subroutine, and (c) subsequently, an assay subroutine. The circuitry enables the nanoporation subroutine only if the verification step successfully verifies the absence of nanopores. Other embodiments are also described.

25 Claims, 17 Drawing Sheets

(56) References Cited

U.S. PATENT DOCUMENTS

2018/0043310 A1    2/2018   Bustamante et al.
2018/0141007 A1    5/2018   Xie et al.

FOREIGN PATENT DOCUMENTS

WO     2016/142925     9/2016
WO     2018/091494     5/2018

OTHER PUBLICATIONS

Sano, Mamiko, et al. "Quantitative Evaluation of Dielectric Breakdown of Silicon Micro-and Nanofluidic Devices for Electrophoretic Transport of a Single DNA Molecule." Micromachines 9.4 (2018): 180.

An Office Action dated Mar. 27, 2019, which issued during the prosecution of United Kingdom Patent Application No. 1815931.9.

Kwok, Harold, Kyle Briggs, and Vincent Tabard-Cossa. "Nanopore fabrication by controlled dielectric breakdown." PloS one 9.3 (2014): e92880.

Bandara, YM Nuwan DY, Buddini I. Karawdeniya, and Jason R. Dwyer. "Push-Button Method To Create Nanopores Using a Tesla-Coil Lighter." ACS Omega 4.1 (2019): 226-230.

Karawdeniya, Buddini I., et al. "Challenging Nanopores with Analyte Scope and Environment." Journal of Analysis and Testing 3.1 (2019): 61-79.

Kuan, Aaron T., et al. "Electrical pulse fabrication of graphene nanopores in electrolyte solution." Applied physics letters 106.20 (2015): 203109.

Roshan, Kamyar, Zifan Tang, and Weihua Guan. "High fidelity moving Z-score based controlled breakdown fabrication of solid-state nanopore." Nanotechnology (2018).

Saharia, Jugal, et al. "Molecular-Level Profiling of Human Serum Transferrin Protein through Assessment of Nanopore-Based Electrical and Chemical Responsiveness." ACS nano 13.4 (2019): 4246-4254.

Karawdeniya, Buddini Iroshika, et al. "Surveying silicon nitride nanopores for glycomics and heparin quality assurance." Nature communications 9.1 (2018): 3278.

Graf, Michael, et al. "Fabrication and practical applications of molybdenum disulfide nanopores." Nature protocols 14.4 (2019): 1130.

Zhang, Yuning, et al. "Nanopore Formation via Tip-Controlled Local Breakdown Using an Atomic Force Microscope." Small Methods (2019): 1900147.

Bello, Julian, et al. "Increased dwell time and occurrence of dsDNA translocation events through solid state nanopores by LiCl concentration gradients." Electrophoresis 40.7 (2019): 1082-1090.

Bello, Julian, and Jiwook Shim. "Solid-state nanopore fabrication in LiCl by controlled dielectric breakdown." Biomedical microdevices 20.2 (2018): 38.

Briggs, Kyle, Harold Kwok, and Vincent Tabard-Cossa. "Automated Fabrication of 2-nm Solid-State Nanopores for Nucleic Acid Analysis." Small 10.10 (2014): 2077-2086.

Briggs, Kyle, et al. "Kinetics of nanopore fabrication during controlled breakdown of dielectric membranes in solution." Nanotechnology 26.8 (2015): 084004.

Briggs, Kyle, et al. "DNA translocations through nanopores under nanoscale preconfinement." Nano letters 18.2 (2017): 660-668.

Lam, Michelle H., et al. "Entropic Trapping of DNA with a Nanofiltered Nanopore." ACS Applied Nano Materials 2.8 (2019): 4773-4781.

Roelen, Zachary, et al. "Instrumentation for low noise nanopore-based ionic current recording under laser illumination." Review of Scientific Instruments 89.1 (2018): 015007.

Waugh, Matthew, et al. "Interfacing solid-state nanopores with gel media to slow DNA translocations." Electrophoresis 36.15 (2015): 1759-1767.

Carlsen, Autumn T., et al. "Solid-state nanopore localization by controlled breakdown of selectively thinned membranes." Nanotechnology 28.8 (2017): 085304.

Goto, Yusuke, et al. "Integrated solid-state nanopore platform for nanopore fabrication via dielectric breakdown, DNA-speed deceleration and noise reduction." Scientific reports 6 (2016): 31324.

Matsui, Kazuma, et al. "Static charge outside chamber induces dielectric breakdown of solid-state nanopore membranes." Japanese Journal of Applied Physics 57.4 (2018): 046702.

Yanagi, Itaru, et al. "Thickness-dependent dielectric breakdown and nanopore creation on sub-10-nm-thick SiN membranes in solution." Journal of Applied Physics 121.4 (2017): 045301.

Yanagi, Itaru, et al. "Two-step breakdown of a SiN membrane for nanopore fabrication: Formation of thin portion and penetration." Scientific reports 8 (2018).

Ying, Cuifeng, et al. "3D nanopore shape control by current-stimulus dielectric breakdown." Applied Physics Letters 109.6 (2016): 063105.

Wang, Yunlong, et al. "Fabrication of multiple nanopores in a SiN x membrane via controlled breakdown." Scientific reports 8.1 (2018): 1234.

He, Feng, et al. "Label-free sensitive detection of Microcystin-LR via aptamer-conjugated gold nanoparticles based on solid-state nanopores." Langmuir 34.49 (2018): 14825-14833.

Yan, Han, et al. "Slowing down DNA translocation velocity using a LiCl salt gradient and nanofiber mesh." European Biophysics Journal 48.3 (2019): 261-266.

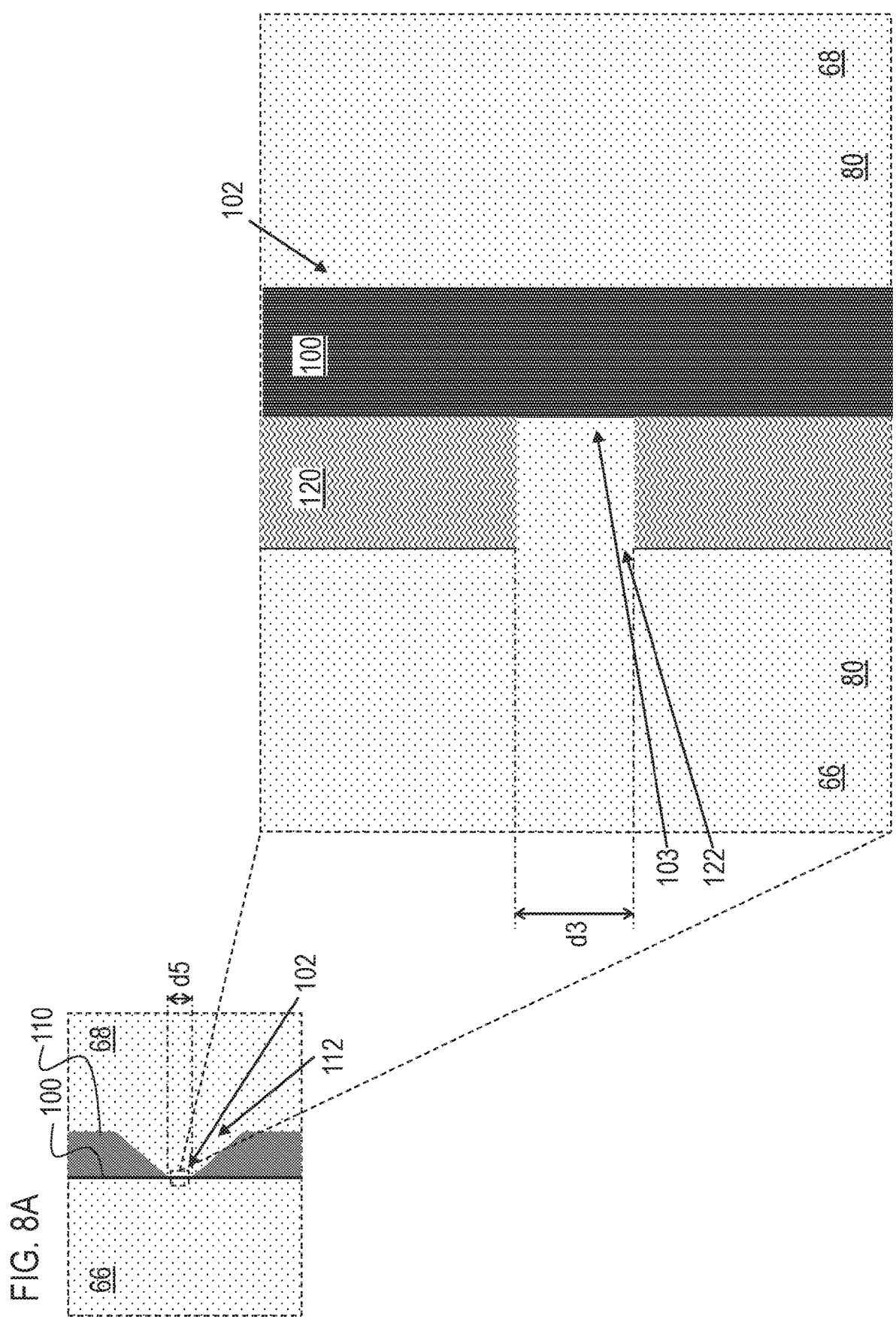

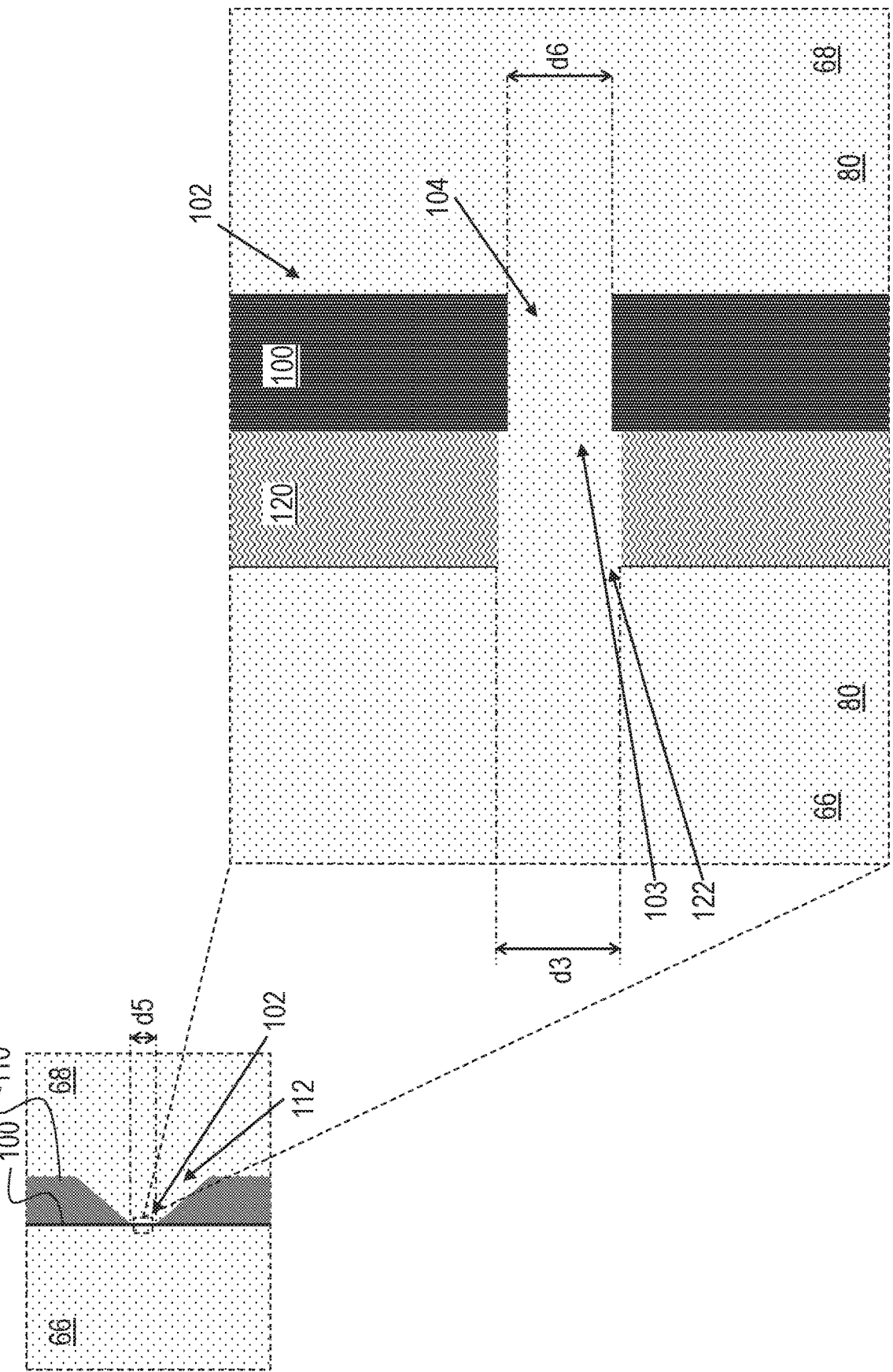

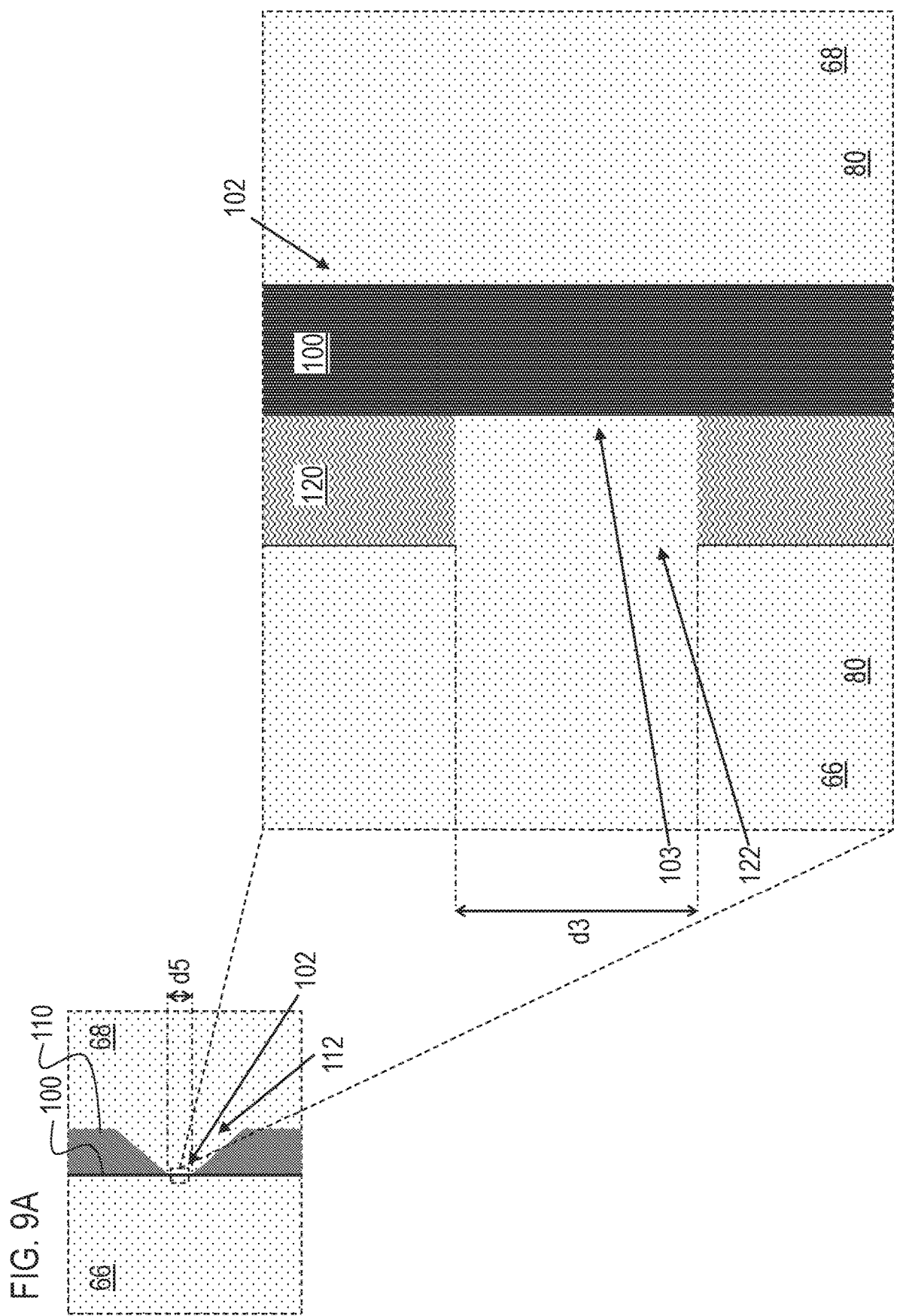

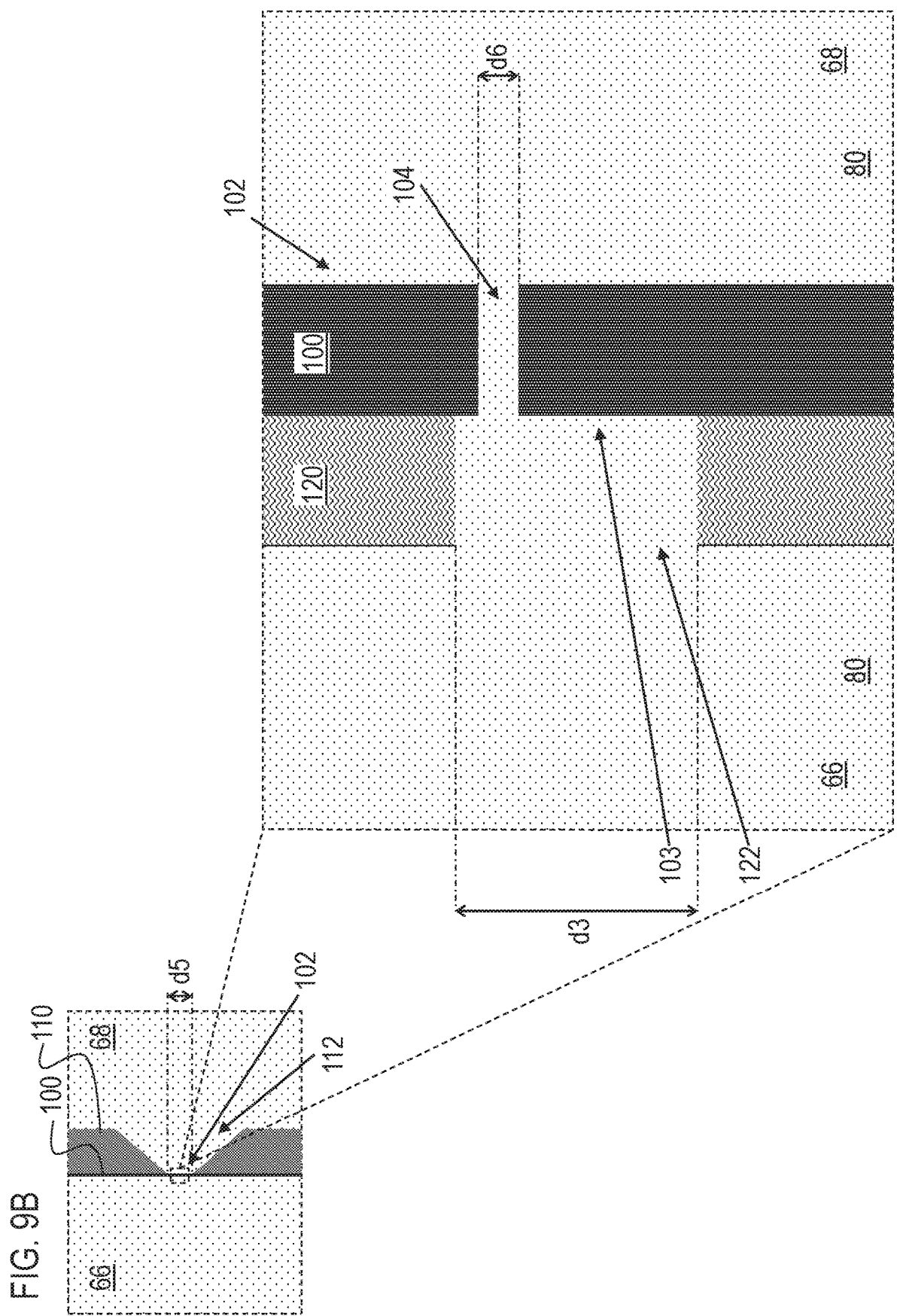

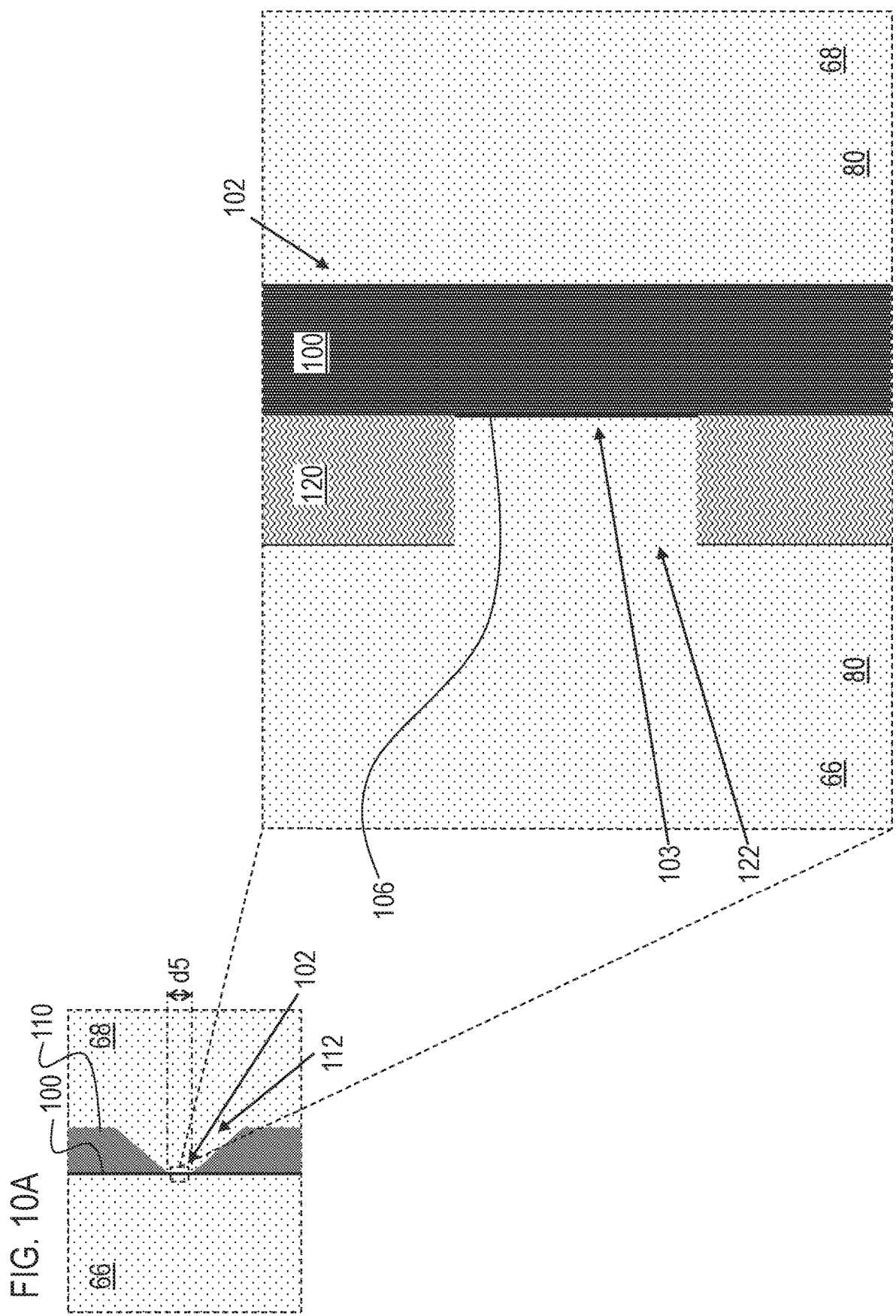

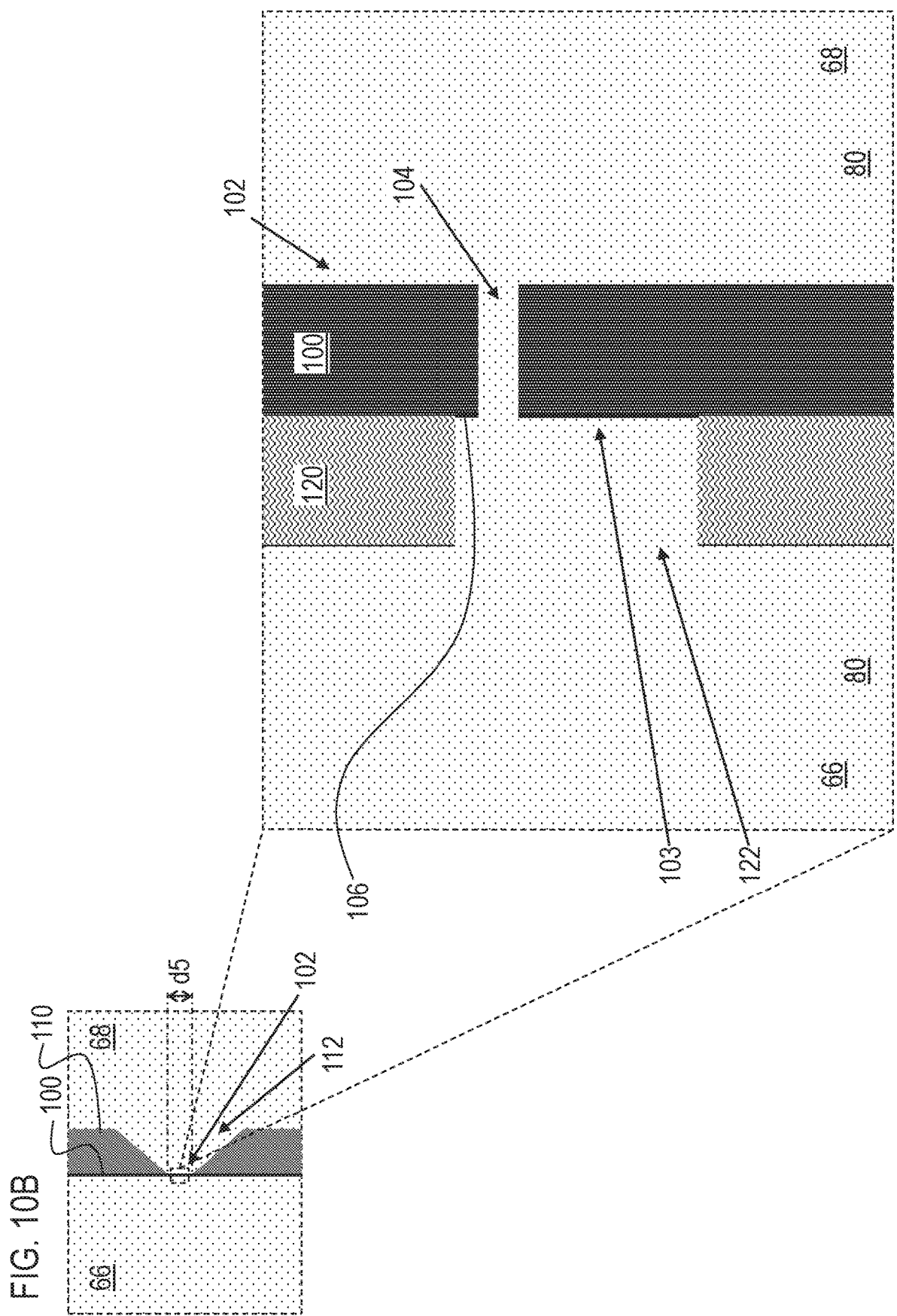

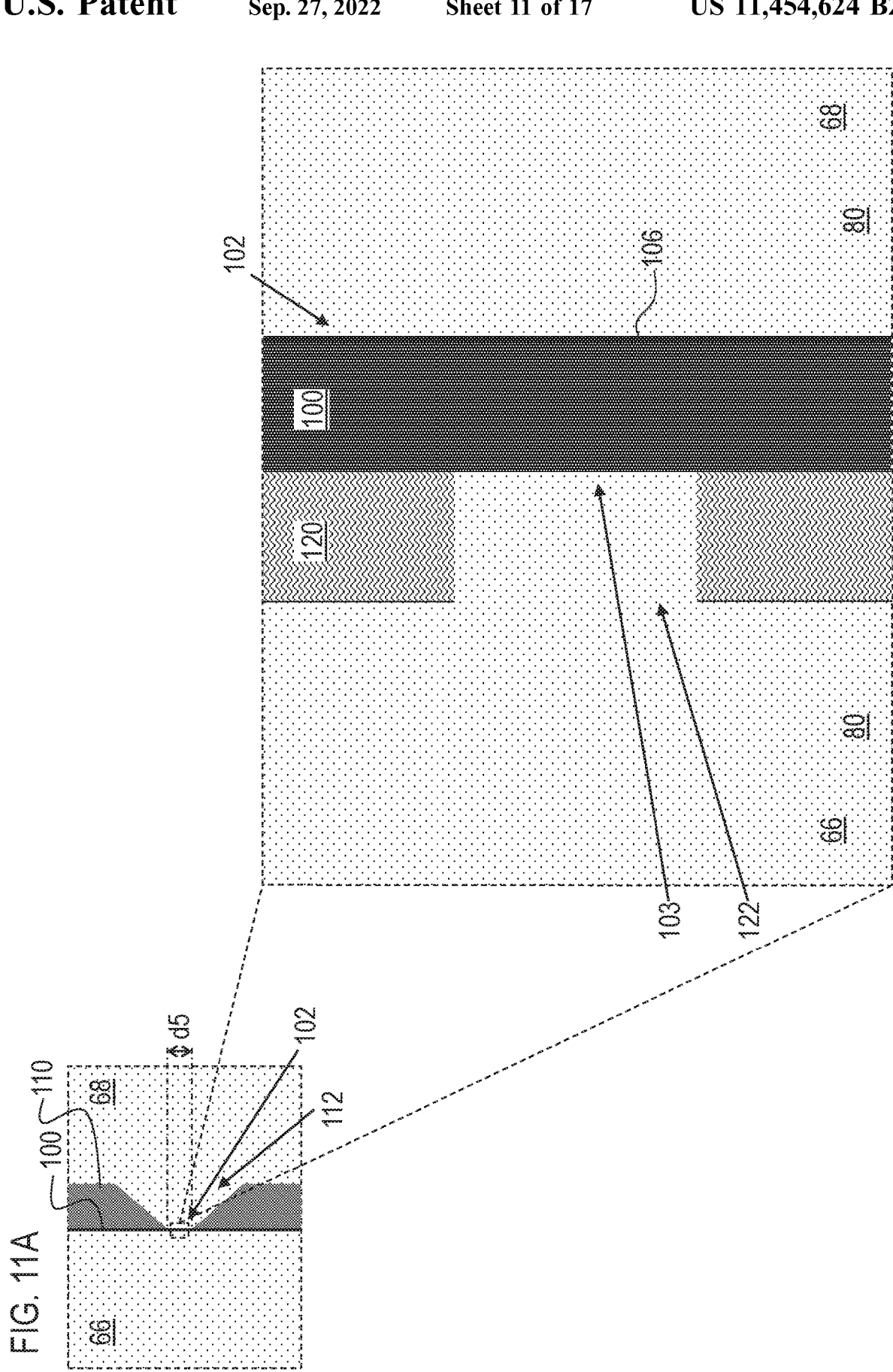

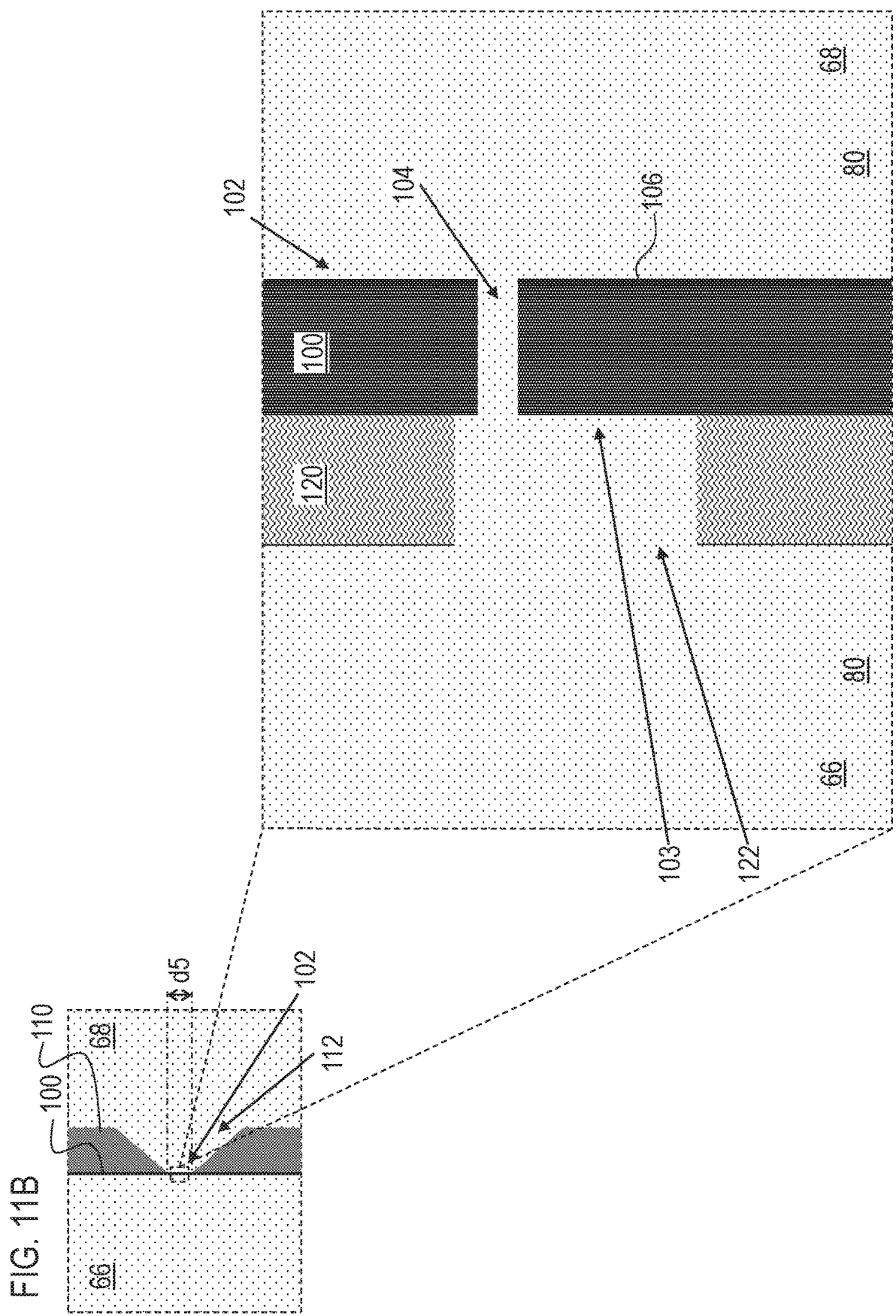

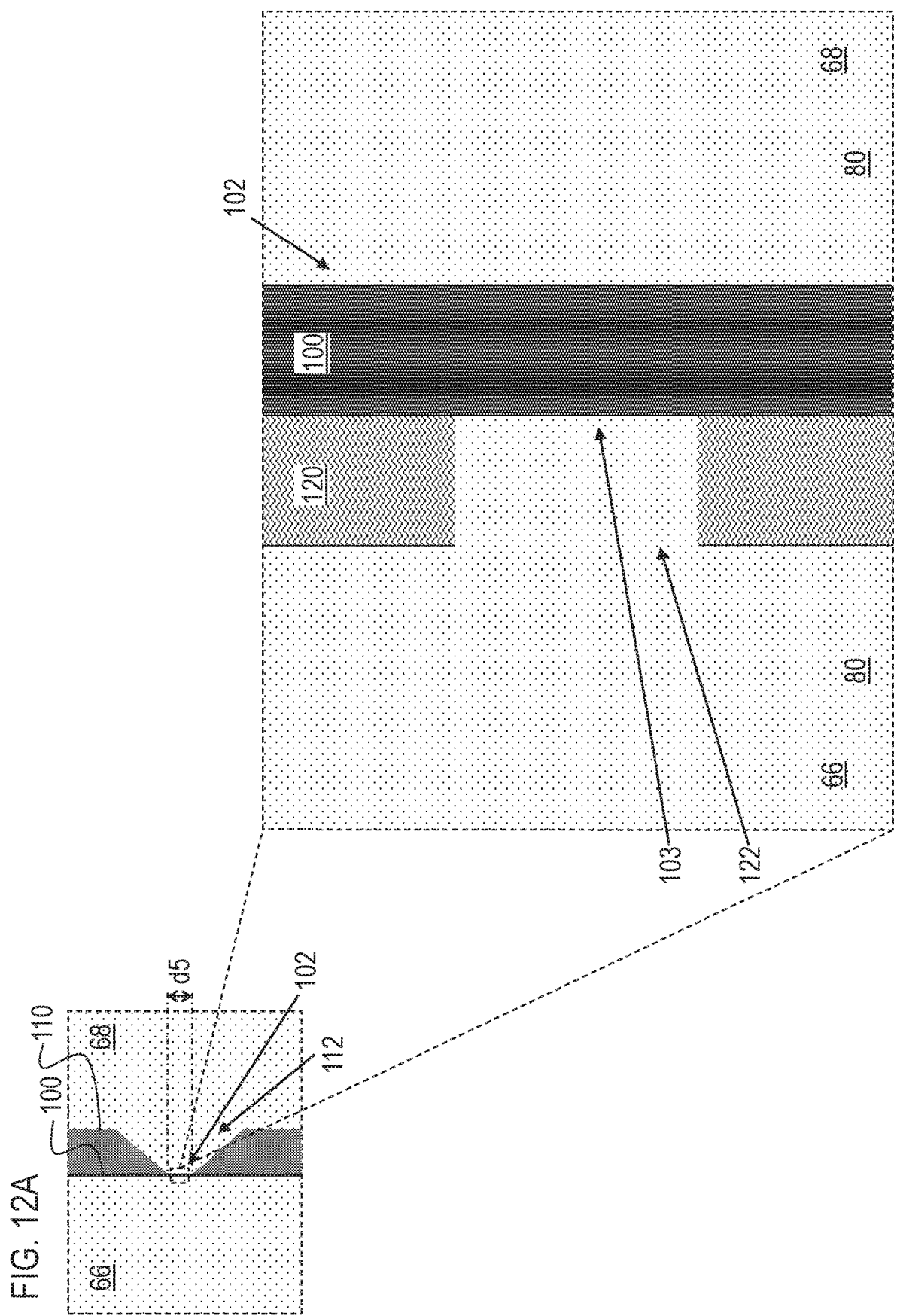

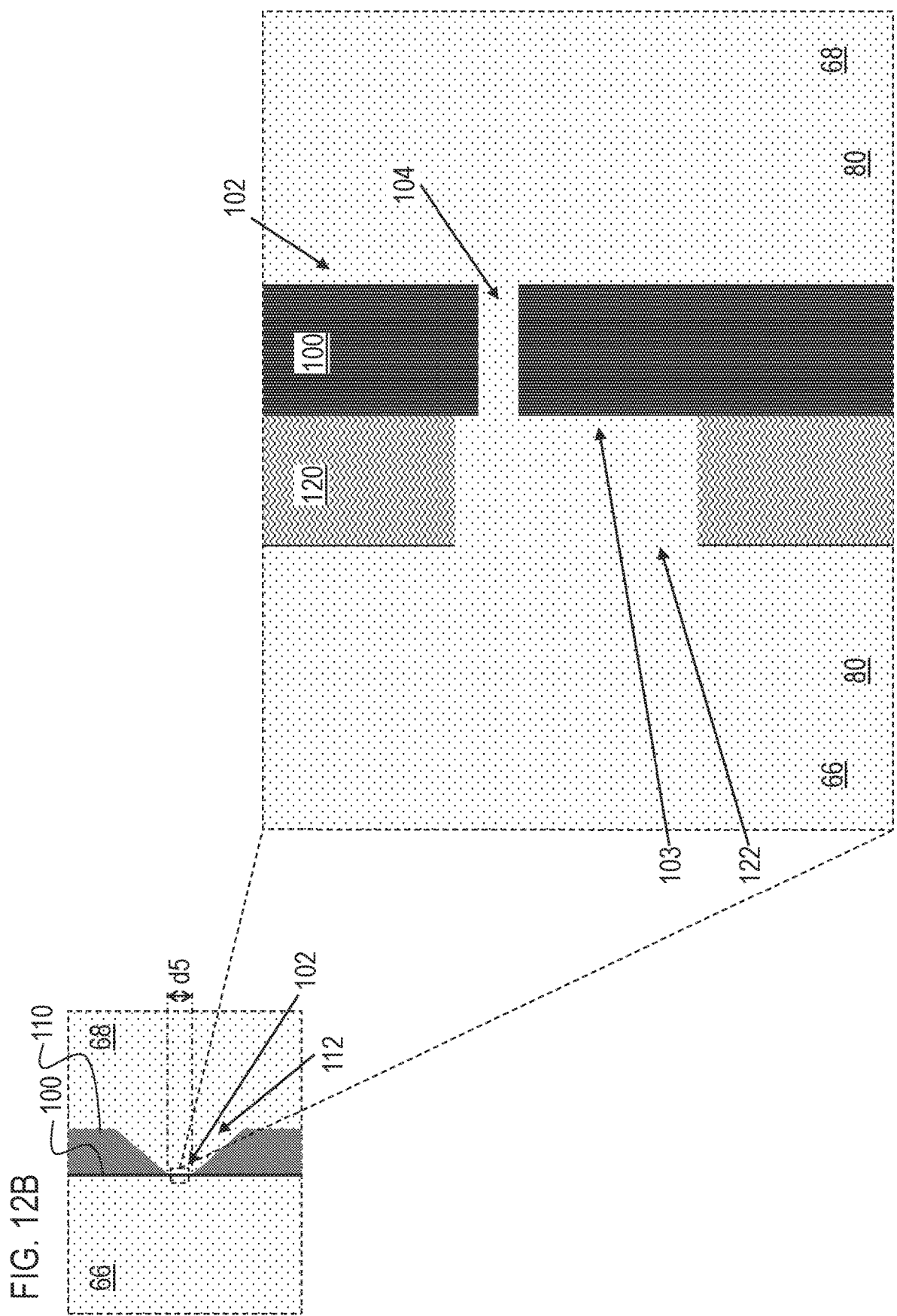

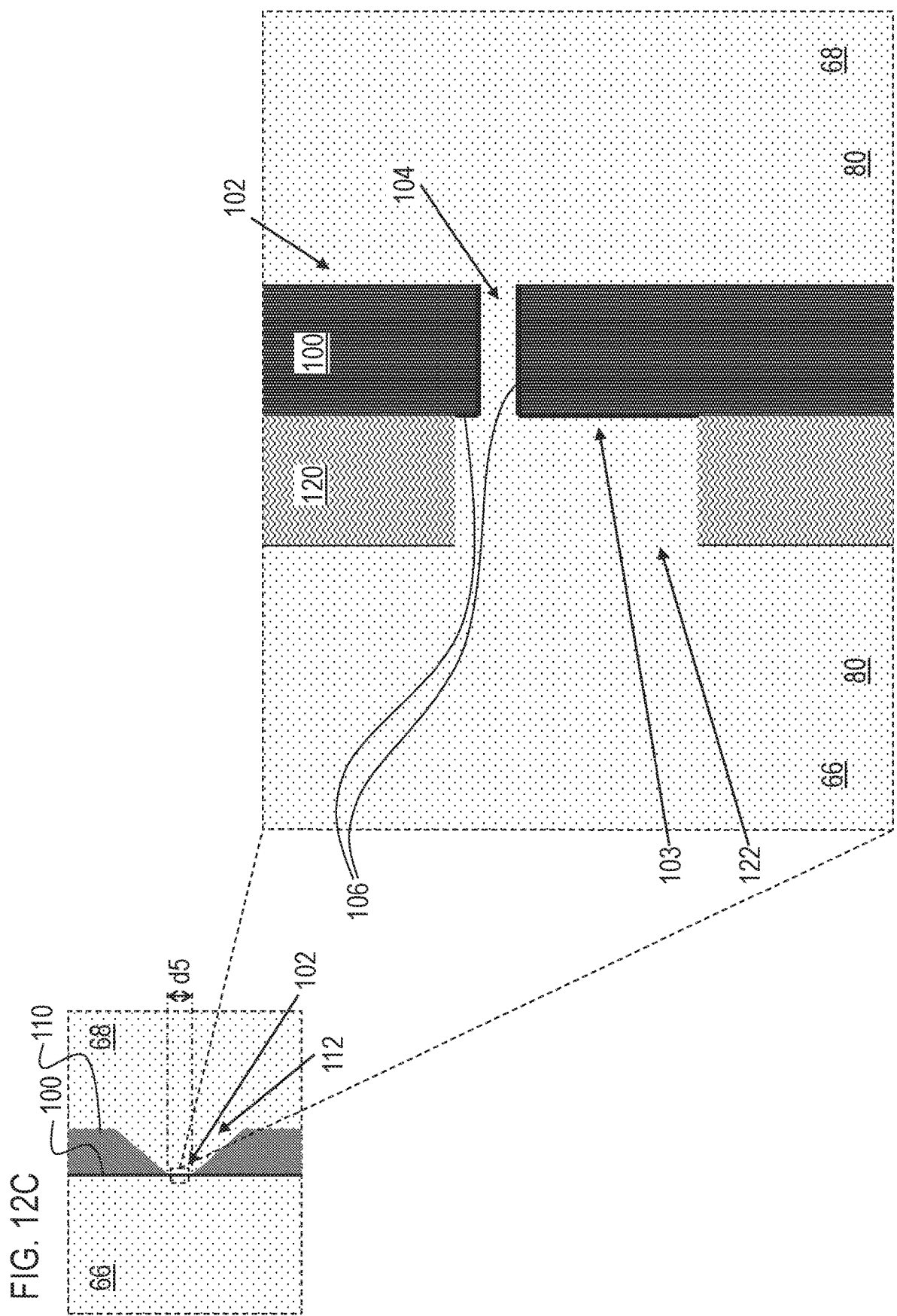

NANOPORE TECHNOLOGIES

CROSS-REFERENCES TO RELATED APPLICATIONS

The present application claims priority from UK Patent Application GB 1815931.9, filed Sep. 28, 2018, which is incorporated herein by reference.

FIELD OF THE INVENTION

Some applications of the present invention relate in general to nanopore-based assays. More specifically, some applications of the present invention relate to apparatus and techniques for forming, optimizing, and using nanopores for nanopore-based assays.

BACKGROUND

Nanopore-based assays involve identification of the translocation of an analyte through a nanopore, by detecting drops in electrical conduction through the nanopore caused by the analyte at least partly obstructing the path of conduction while disposed in the nanopore. Typically, the translocation is achieved by driving a translocation current through the nanopore.

SUMMARY OF THE INVENTION

Devices and test cartridges for nanopore-based assays are described. The test cartridges comprise a membrane. For some applications, the devices and test cartridges are configured specifically to both (i) form a nanopore in the membrane, and (ii) subsequently perform nanopore-based assaying using the newly-formed nanopore.

The test cartridges are typically provided with the membrane intact (i.e., containing no nanopores), and nanoporation must therefore be performed prior to assaying. For some applications, apparatus is configured to verify that the membrane is, in fact, initially intact before proceeding.

Formation of the nanopore is typically achieved by application of a nanoporation (e.g., ablating) energy. For example, electrical energy may be provided in the form of a nanoporation voltage applied between electrodes on either side of the membrane, in order to effect nanoporation via dielectric breakdown (DB) of the membrane.

For some applications, a protective film with an aperture is provided on the membrane to guide and/or improve formation of the nanopore.

For some applications, a surface of the membrane is chemically modified (e.g., to affect the translocation of the analyte through the nanopore). For some such applications, the surface is modified only at the aperture in the protective film.

Typically, the nanopore-based assays are for detection of an analyte in a sample. The analyte is typically detected via monitoring of electrical conduction through the nanopore, the conduction being transiently inhibited by the presence of the analyte translocating through the nanopore. The translocation is typically mediated by application of a voltage between electrodes on either side of the membrane.

During nanoporation, the magnitude of the voltage applied across the membrane is typically changed. For some applications, the monitoring of the electrical conduction through the nanopore is paused for a buffer period when the voltage magnitude is changed, in order to reduce the likelihood of capacitive current, induced by the change in voltage magnitude, being misread by the device as an ionic current indicative of successful nanopore formation.

For some applications, the test cartridges include an on-board positive-control moiety that serves as a positive control for the target analyte, in order to improve the accuracy and/or quantitativeness of the assay.

There is therefore provided, in accordance with an application of the present invention, apparatus for use with a sample suspected of containing an analyte, the apparatus including:
  a test cartridge, including:
    a casing that defines an internal space;
    a membrane having a thickness of 0.1 nm-1 micron, the membrane disposed inside the casing, separating the internal space into a sample chamber and a second chamber, and fluidically and electrically isolating the second chamber from the sample chamber, and the casing shaped to define a port via which the sample is introducible into the sample chamber,
    a first electrode, disposed within the sample chamber;
    a first cartridge-terminal, electrically connected to the first electrode, and accessible from outside of the cartridge;
    a second electrode, disposed within the second chamber;
    a second cartridge-terminal, electrically connected to the second electrode, and accessible from outside of the cartridge; and
  a device for use with the test cartridge, the device including:
    a dock, including a first dock-terminal and a second dock-terminal, and configured to receive the cartridge such that docking of the cartridge with the dock places the first and second cartridge-terminals in electrical contact with the first and second dock-terminals; and
    circuitry, electrically connected to the cartridge-terminals, and the circuitry is configured to perform, while the cartridge remains docked with the dock:
      (a) a nanoporation subroutine, in which the circuitry:
        (i) applies nanoporation energy to the membrane, the nanoporation energy configured to ablate a nanopore in the membrane, and
        (ii) monitors conduction of a pore-detection current between the first and second electrodes, and
        (iii) ends the nanoporation subroutine upon detecting that the pore-detection current exceeds a threshold amplitude, the threshold amplitude being indicative of successful formation of a nanopore, and
      (b) subsequently, an assay subroutine, in which the circuitry:
        (i) applies an assay voltage between the first and second electrodes, the assay voltage having a magnitude of 0.01-5 V, and
        (ii) while driving the assay voltage, simultaneously monitors electrical conduction between at least two of the dock-terminals.

In an application, the membrane is a solid-state membrane.

In an application, the membrane is a biological membrane.

In an application, the membrane is a block copolymer membrane.

In an application, the cartridge includes a positive-control moiety having a known concentration, disposed in the internal space, the positive-control moiety being a positive control for the analyte.

In an application, the circuitry is configured such that steps (i) and (ii) of the nanoporation subroutine are performed iteratively.

In an application, the circuitry is configured such that steps (i) and (ii) of the nanoporation subroutine are performed simultaneously.

In an application, the circuitry is configured to apply a pore-detection voltage between the first and second electrodes during the nanoporation subroutine, the pore-detection current resulting from the application of the pore-detection voltage.

In an application, the nanoporation energy is a nanoporation voltage, the circuitry being configured to apply the nanoporation voltage between the first and second electrodes during the nanoporation subroutine, the pore-detection current resulting from the application of the nanoporation voltage.

In an application, the circuitry is configured to perform, prior to performing the nanoporation subroutine and the assay subroutine, a verification step during which the circuitry verifies an attribute of the cartridge.

In an application, the circuitry is configured to require that the attribute be successfully verified between (i) docking of the cartridge with the dock, and (ii) performing the nanoporation subroutine.

In an application, the circuitry is configured:
to detect undocking of the cartridge from the dock, and
to require, if the cartridge (i) becomes undocked from the dock after the attribute has been successfully verified, and (ii) is subsequently re-docked with the dock, that the verification step be re-performed between (i) the re-docking and (ii) performing the nanoporation subroutine and the assay subroutine.

In an application, the attribute is an absence of nanopores in the membrane, and the circuitry is configured to perform the verification step during which the circuitry verifies an absence of nanopores in the membrane.

In an application, the circuitry is configured to perform the verification step by monitoring conduction between the first and second electrodes.

In an application, the circuitry is configured to perform the verification step by applying a pore-detection voltage between the electrodes, and to monitor conduction, between the first and second electrodes, of a pore-detection current resulting from the pore-detection voltage.

In an application, the apparatus further includes a user interface, and the circuitry is configured to determine a concentration of the analyte in the sample by analyzing data indicative of the electrical conduction monitored during the assay subroutine, and to responsively drive the user interface to display information indicative of the concentration of the analyte.

In an application, the circuitry is configured to display the information qualitatively.

In an application, the circuitry is configured to display the information quantitatively.

In an application, the user interface is a component of the device.

In an application, the user interface includes a display.

In an application, the device includes a computer interface, and the circuitry is configured to output the data to the user interface via the computer interface, the user interface being provided by software on a general-purpose computer.

In an application, the circuitry is further configured to perform, while the cartridge remains docked with the dock, a positive-control subroutine in which the circuitry:
(i) applies the assay voltage between the first and second electrodes, and
(ii) while driving the assay voltage, simultaneously monitors electrical conduction between at least two of the dock-terminals.

In an application, the cartridge includes a positive-control moiety having a known concentration, disposed in the internal space, the positive-control moiety being a positive control for the analyte.

In an application, the circuitry is configured to determine a concentration of the analyte in the sample by analyzing (i) data indicative of the electrical conduction monitored during the assay subroutine, and (ii) data indicative of the electrical conduction monitored during the positive-control subroutine.

In an application, the nanoporation energy is a nanoporation voltage, the circuitry being configured to apply the nanoporation voltage between the first and second electrodes.

In an application, the circuitry is configured to apply the nanoporation voltage at a magnitude of 0.01-100 V.

In an application, the nanoporation energy is electromagnetic radiation energy, the circuitry being configured to apply the electromagnetic radiation energy to the membrane.

In an application, the device includes an electromagnetic radiation source, the cartridge includes an optical fiber, and the circuitry is configured to apply the electromagnetic radiation energy by driving the electromagnetic radiation source to radiate the electromagnetic radiation energy through the optical fiber.

In an application, the nanoporation energy is acoustic energy, the circuitry being configured to apply the acoustic energy to the membrane.

In an application, the device includes an acoustic energy source, and the circuitry is configured to apply the acoustic energy by driving the acoustic energy source.

In an application, the acoustic energy is ultrasound energy, the circuitry being configured to apply the ultrasound energy to the membrane.

In an application, the cartridge further includes a protective film coating a surface of the membrane, the film shaped to define an aperture through the film such that a target region of the surface is exposed through the aperture, the protective film configured to insulate the membrane from the nanoporation energy except for at the aperture, thereby biasing formation of the nanopore to the target region.

In an application, the film is an electrically-insulating film.

In an application, the film has a thickness of 1 nm-10 microns.

In an application, a sample-side of the membrane faces the sample chamber, and a second-side of the membrane faces the second chamber, and the film is disposed on the sample-side of the membrane.

In an application, a sample-side of the membrane faces the sample chamber, and a second-side of the membrane faces the second chamber, and the film is disposed on the second-side of the membrane.

In an application, the film is shaped such that the aperture has a width of 0.001-1 micron.

In an application, the film is shaped such that the aperture has a width of 0.1-10 microns.

In an application, the cartridge further includes a support on which the membrane is disposed, the support supporting the membrane and being shaped to define a window through which a zone of the membrane is exposed.

In an application, a width of the aperture is smaller than a width of the window.

In an application, the support is shaped such that the window has a width of 1-500 microns.

In an application:

the surface is a first surface of the membrane on a first side of the membrane, and the film coats the first surface of the membrane such that the target region is on the first surface of the membrane, and the support is disposed against a second surface of the membrane on a second side of the membrane that is opposite the first side of the membrane, such that the zone of the membrane is on the second side of the membrane.

In an application, aperture and the window are positioned such that the target region is aligned with the zone.

In an application:

the surface is a first surface of the membrane on a first side of the membrane, the support is disposed against the first side of the membrane, and the film coats the first surface of the membrane within the zone, such that the target region is on the first surface of the membrane within the zone.

In an application, the membrane is a silicon-based membrane, and the support includes silicon.

In an application, the membrane is a silicon-based membrane.

In an application, the membrane is a 2D-material-based membrane.

In an application, the aperture is exactly one aperture, and the film is shaped to define the exactly one aperture.

In an application, chemistry of the surface at the target region is modified by a chemical moiety that is bound to the surface only at the target region.

There is further provided, in accordance with an application of the present invention, apparatus for use with a test cartridge, including:

a dock, configured to receive the test cartridge;

a plurality of dock-terminals, positioned with respect to the dock so as to become electrically contacted with the test cartridge upon the dock receiving the test cartridge; and circuitry, configured to perform:
(a) a nanoporation subroutine, in which the circuitry iteratively:
(i) applies a nanoporation voltage between at least two of the dock-terminals, the nanoporation voltage typically having a magnitude of 1-100 V, and
(ii) applies a pore-detection voltage between at least two of the dock-terminals, and detects conduction of a pore-detection current resulting from the applied pore-detection voltage, the pore-detection voltage typically having a magnitude of 10-900 mV,
until the detected conduction is above a threshold amplitude, and
(b) an assay subroutine, in which the circuitry:
(i) applies a translocation voltage between at least two of the dock-terminals, the translocation voltage typically having a magnitude of 0.01-5 V, and
(ii) while driving the translocation voltage, simultaneously monitors electrical conduction between at least two of the dock-terminals.

There is further provided, in accordance with an application of the present invention, apparatus, including:

a membrane having a thickness of 0.1 nm-1 micron; and an electrically-insulating film having a thickness of 1 nm-10 microns, coating a surface of the membrane, and shaped to define an aperture through the film, such that a target region of the surface is exposed through the aperture.

In an application, the membrane is a solid-state membrane.

In an application, the membrane is a biological membrane.

In an application, the membrane is a block copolymer membrane.

In an application, the film is shaped such that the aperture has a width of 0.001-1 micron.

In an application, the film is shaped such that the aperture has a width of 0.1-10 microns.

In an application, the membrane is a silicon-based membrane, and the support includes silicon.

In an application, the membrane is a silicon-based membrane.

In an application, the membrane is a 2D-material-based membrane.

In an application, the aperture is exactly one aperture, and the film is shaped to define the exactly one aperture.

In an application, the apparatus further includes:

a casing that defines an internal space, the membrane disposed inside the casing, and separating the internal space into a sample chamber and a second chamber, the membrane fluidically and electrically isolating the second chamber from the sample chamber, and the casing shaped to define a port via which a sample is introducible into the sample chamber, a first electrode, disposed within the sample chamber;

a first cartridge-terminal, electrically connected to the first electrode, and accessible from outside of the cartridge;

a second electrode, disposed within the second chamber; and a second cartridge-terminal., electrically connected to the second electrode, and accessible from outside of the cartridge.

In an application, a sample-side of the membrane faces the sample chamber, and a second-side of the membrane faces the second chamber, and the film is disposed on the sample-side of the membrane.

In an application, a sample-side of the membrane faces the sample chamber, and a second-side of the membrane faces the second chamber, and the film is disposed on the second-side of the membrane.

In an application, the apparatus further includes a support on which the membrane is disposed, the support supporting the membrane and being shaped to define a window through which a zone of the membrane is exposed.

In an application, a width of the aperture is smaller than a width of the window.

In an application, the support is shaped such that the window has a width of 1-500 microns.

In an application:

the surface is a first surface of the membrane on a first side of the membrane, and the film coats the first surface of the membrane such that the target region is on the first surface of the membrane, and the support is disposed against a second surface of the membrane on a second side of the membrane that is opposite the first side of the membrane, such that the zone of the membrane is on the second side of the membrane.

In an application, aperture and the window are positioned such that the target region is aligned with the zone.

In an application:

the surface is a first surface of the membrane on a first side of the membrane, the support is disposed against the first side of the membrane, and the film coats the first surface of the membrane within the zone, such that the target region is on the first surface of the membrane within the zone.

In an application, chemistry of the surface at the target region is modified by a chemical moiety that is bound to the surface only at the target region.

In an application, the chemical moiety is silane.

In an application, the chemical moiety is a thiol.

In an application, the chemical moiety is an amino acid.

In an application, the chemical moiety is a carboxylic acid.

In an application, the chemical moiety is an azide.

In an application, the chemical moiety is an amide.

In an application, the chemical moiety is a sugar.

In an application, the chemical moiety is an immunoglobulin.

In an application, the chemical moiety is a nucleic acid.

In an application, the chemical moiety is an oligonucleotide.

In an application, the chemical moiety is an aptamer.

In an application, the chemical moiety is a peptide nucleic acid.

In an application, the chemistry of the surface is modified to have increased hydrophilicity.

In an application, the chemistry of the surface is modified to have decreased hydrophilicity.

In an application, the chemistry of the surface is modified to have an increased affinity for immunoglobulins.

In an application, the chemistry of the surface is modified to have an increased affinity for nucleic acids.

In an application, the chemistry of the surface is modified to have an increased affinity for nucleic acids having a particular sequence.

In an application, the chemistry of the surface is modified to have an increased affinity for sugars.

In an application, the chemistry of the surface is modified to have an increased affinity for polypeptides.

In an application, the chemistry of the surface is modified to have an increased affinity for aldehydes.

In an application, the chemistry of the surface is modified to have an increased affinity for ketones.

In an application, the chemistry of the surface is modified to have an increased affinity for alkynes.

In an application, the chemistry of the surface is modified to have an increased affinity for azides.

In an application, the chemistry of the surface is modified to have an increased affinity for esters.

In an application, the chemistry of the surface is modified to have an increased affinity for carboxyls.

In an application, the chemistry of the surface is modified to have an increased affinity for boric acid.

In an application, the chemistry of the surface is modified to have an increased affinity for methoxyethene.

In an application, the chemistry of the surface is modified to have an increased affinity for epoxies.

There is further provided, in accordance with an application of the present invention, apparatus, including:

a membrane having a thickness of 0.1 nm-1 micron, the membrane being susceptible to ablation by application of an energy; and a casing that defines an internal space, the membrane disposed inside the casing, and separating the internal space into a sample chamber and a second chamber, the membrane fluidically and electrically isolating the second chamber from the sample chamber, and the casing shaped to define a port via which a sample is introducible into the sample chamber, a first electrode, disposed within the sample chamber;

a first cartridge-terminal, electrically connected to the first electrode, and accessible from outside of the cartridge;

a second electrode, disposed within the second chamber;

a second cartridge-terminal, electrically connected to the second electrode, and accessible from outside of the cartridge; and a protective film having a thickness of 1 nm-10 microns, coating a surface of the membrane, shaped to define exactly one aperture through the film such that a target region of the surface is exposed through the aperture, and configured to protect the membrane from the energy except for at the aperture.

In an application, the membrane is a solid-state membrane.

In an application, the membrane is a biological membrane.

In an application, the membrane is a block copolymer membrane.

In an application, a sample-side of the membrane faces the sample chamber, and a second-side of the membrane faces the second chamber, and the film is disposed on the sample-side of the membrane.

In an application, a sample-side of the membrane faces the sample chamber, and a second-side of the membrane faces the second chamber, and the film is disposed on the second-side of the membrane.

In an application, the film is shaped such that the aperture has a width of 0.001-1 micron.

In an application, the film is shaped such that the aperture has a width of 0.1-10 microns.

In an application, the membrane is a silicon-based membrane, and the support includes silicon.

In an application, the membrane is a silicon-based membrane.

In an application, the membrane is a 2D-material-based membrane.

In an application, the energy is electrical energy, and the film is an electrically-insulating film.

In an application, the first electrode, the first cartridge-terminal, the second electrode, and the second cartridge-terminal are configured to facilitate ablation of the membrane at the aperture via application of the electrical energy.

In an application, the apparatus further includes a support on which the membrane is disposed, the support supporting the membrane and being shaped to define a window through which a zone of the membrane is exposed.

In an application, a width of the aperture is smaller than a width of the window.

In an application, the support is shaped such that the window has a width of 1-500 microns.

In an application:

the surface is a first surface of the membrane on a first side of the membrane, and the film coats the first surface of the membrane such that the target region is on the first surface of the membrane, and the support is disposed against a second surface of the membrane on a second side of the membrane that is opposite the first side of the membrane, such that the zone of the membrane is on the second side of the membrane.

In an application, aperture and the window are positioned such that the target region is aligned with the zone.

In an application:

the surface is a first surface of the membrane on a first side of the membrane, the support is disposed against the first side of the membrane, and the film coats the first surface of the membrane within the zone, such that the target region is on the first surface of the membrane within the zone.

In an application, chemistry of the surface at the target region is modified by a chemical moiety that is bound to the surface only at the target region.

In an application, the chemical moiety is silane.

In an application, the chemical moiety is a thiol.

In an application, the chemical moiety is an amino acid.

In an application, the chemical moiety is a carboxylic acid.

In an application, the chemical moiety is an azide.

In an application, the chemical moiety is an amide.

In an application, the chemical moiety is a sugar.

In an application, the chemical moiety is an immunoglobulin.

In an application, the chemical moiety is a nucleic acid.

In an application, the chemical moiety is an oligonucleotide.

In an application, the chemical moiety is an aptamer.

In an application, the chemical moiety is a peptide nucleic acid.

In an application, the chemistry of the surface is modified to have increased hydrophilicity.

In an application, the chemistry of the surface is modified to have decreased hydrophilicity.

In an application, the chemistry of the surface is modified to have an increased affinity for immunoglobulins.

In an application, the chemistry of the surface is modified to an increased affinity for nucleic acids.

In an application, the chemistry of the surface is modified to have an increased affinity for nucleic acids having a particular sequence.

In an application, the chemistry of the surface is modified to have an increased affinity for sugars.

In an application, the chemistry of the surface is modified to an increased affinity for polypeptides.

In an application, the chemistry of the surface is modified to have an increased affinity for aldehydes.

In an application, the chemistry of the surface is modified to have an increased affinity for ketones.

In an application, the chemistry of the surface is modified to an increased affinity for alkynes.

In an application, the chemistry of the surface is modified to have an increased affinity for azides.

In an application, the chemistry of the surface is modified to have an increased affinity for esters.

In an application, the chemistry of the surface is modified to have an increased affinity for carboxyls.

In an application, the chemistry of the surface is modified to have an increased affinity for boric acid.

In an application, the chemistry of the surface is modified to have an increased affinity for methoxyethene.

In an application, the chemistry of the surface is modified to have an increased affinity for epoxies.

There is further provided, in accordance with an application of the present invention, apparatus for use with a sample, the apparatus including a test cartridge that includes:

a casing that defines an internal space;

a membrane that:

has a thickness of less than 1 micron, is disposed inside the casing, and separates the internal space into a sample chamber and a second chamber, fluidically and electrically isolating the second chamber from the sample chamber, the casing being shaped to define a port via which the sample is introducible into the sample chamber, a seal, sealing the port;

a first electrode, disposed within the sample chamber;

a first cartridge-terminal, electrically connected to the first electrode, and accessible from outside of the cartridge;

a second electrode, disposed within the second chamber;

a second cartridge-terminal, electrically connected to the second electrode, and accessible from outside of the cartridge, and:

in the presence of the seal, the sample chamber and the second chamber are each hermetically sealed, and in the absence of the seal, the sample chamber is fluidically accessible from outside of the casing via the port, but the second chamber remains hermetically sealed.

In an application, the membrane is a solid-state membrane.

In an application, the membrane is a biological membrane.

In an application, the membrane is a block copolymer membrane.

In an application, the apparatus further includes a sealed packaging in which the test cartridge is disposed.

In an application, a sample-side of the membrane faces the sample chamber, a second-side of the membrane faces the second chamber, and surface chemistry of the membrane is modified by a chemical moiety that is bound to the membrane only on the second side.

In an application, the apparatus further includes a film having a thickness of 1 nm-10 microns, coating a surface of the membrane, and shaped to define an aperture through the film, such that a target region of the surface is exposed through the aperture.

In an application, the film is an electrically-insulating film.

In an application, the film is disposed on a side of the membrane that faces the sample chamber.

In an application, the film is disposed on a side of the membrane that faces the second chamber.

In an application, chemistry of the surface at the target region is modified by a chemical moiety that is bound to the surface only at the target region.

There is further provided, in accordance with an application of the present invention, a method for detecting an analyte within a sample, the method including:

docking a test cartridge with a dock of a device such that, while the cartridge is docked with the device, (i) at least one first cartridge-terminal of the cartridge is in electrical contact with at least one first dock-terminal of the device, and (ii) at least one second cartridge-terminal of the cartridge is in electrical contact with at least one second dock-terminal of the device, the test cartridge including:

a casing that defines an internal space, a membrane that separates the internal space into a sample chamber and a second chamber, fluidically and electrically isolating the second chamber from the sample chamber, at least one first electrode, disposed within the sample chamber, and electrically connected to the at least one first cartridge-terminal, and at least one second electrode, disposed within the second chamber, and electrically connected to the at least one second cartridge-terminal;

loading the sample into the sample chamber via a sample port that is defined by the casing; and while the cartridge remains docked with the device, activating the device to, via the electrical contact between (i) the at least one first dock-terminal and the at least one first cartridge-terminal, and (ii) the at least one second dock-terminal and the at least one second cartridge-terminal:

form a nanopore in the membrane by applying a nanoporation energy to the membrane, and subsequently:

apply an assay voltage between (i) the at least one first electrode and (ii) the at least one second electrode, the assay voltage having a magnitude of 0.01-5 V, and detect translocation of the analyte through the nanopore by detecting changes in electrical conduction between the electrodes via the nanopore.

There is further provided, in accordance with an application of the present invention, apparatus, including:

a dock;

a first dock-terminal positioned at the dock and a second dock-terminal positioned at the dock; and circuitry, configured to:

perform a subroutine in which the circuitry automatically:

applies a voltage between the first and second dock-terminals, periodically changes a magnitude of the voltage, and monitors conduction of a current between the first and second dock-terminals, and automatically stop the subroutine in response to detecting that an amplitude of the current exceeds a threshold amplitude, and the circuitry is provided to apply a buffer period after changing the magnitude of the voltage, and to ignore the current during the buffer period, such that the circuitry does not automatically stop the subroutine in response to the amplitude exceeding the threshold amplitude during the buffer period.

In an application, the apparatus further includes a test cartridge configured to be docked to the dock, the test cartridge including:

a membrane having a thickness of 0.1 nm-1 micron; and a casing that defines an internal space, the membrane disposed inside the casing, and separating the internal space into a sample chamber and a second chamber, the membrane fluidically and electrically isolating the second chamber from the sample chamber, and the casing shaped to define a port via which a sample is introducible into the sample chamber, a first electrode, disposed within the sample chamber;

a second electrode, disposed within the second chamber;

a first cartridge-terminal, electrically connected to the first electrode; and, a second cartridge-terminal, electrically connected to the second electrode, and:

the first and second cartridge-terminals are accessible from outside of the cartridge such that docking of the test cartridge to the dock places the first and second cartridge-terminals in electrical contact with the first and second dock-terminals, and while the cartridge is docked with the dock:

the circuitry is configured to create a nanopore in the membrane by applying the voltage, and the circuitry is configured to detect the nanopore in the membrane by monitoring the conduction.

There is further provided, in accordance with an application of the present invention, apparatus for facilitating nanopore-based detection of an analyte in a sample, the apparatus including:

a casing that defines an internal space;

a membrane having a thickness of 0.1 nm-1 micron, the membrane disposed inside the casing, and separating the internal space into a sample chamber and a second chamber, and the casing shaped to define a port via which the sample is introducible into the sample chamber, a first electrode, disposed within the sample chamber;

a first cartridge-terminal, electrically connected to the first electrode, and accessible from outside of the cartridge:

a second electrode, disposed within the second chamber;

a second cartridge-terminal, electrically connected to the second electrode, and accessible from outside of the cartridge; and a positive-control moiety having a known concentration, disposed in the internal space, the positive-control moiety being a positive control for the analyte.

In an application, the membrane is a solid-state membrane.

In an application, the membrane is a biological membrane.

In an application, the membrane is a block copolymer membrane.

In an application, the positive-control moiety is disposed in the sample chamber.

In an application, the positive-control moiety is disposed in the second chamber.

In an application, the membrane fluidically and electrically isolates the second chamber from the sample chamber.

In an application, the membrane is shaped to define a nanopore between the sample chamber and the second chamber, and dimensioned to facilitate translocation of the positive-control moiety through the nanopore.

In an application, the apparatus includes a kit that includes:

a test cartridge that includes the casing, the membrane, the first and second electrodes, the first and second cartridge-terminals, and the positive-control moiety; and at least one nucleic acid primer appropriate for amplification of the analyte.

In an application, the kit further includes a polymerase.

In an application, the apparatus further includes at least one nucleic acid primer appropriate for amplification of the analyte, the at least one nucleic acid primer disposed in the internal space.

In an application, the at least one nucleic acid primer is disposed in the sample chamber.

In an application, the apparatus further includes a polymerase disposed in the internal space.

In an application, the at least one polymerase is disposed in the sample chamber.

There is therefore provided, in accordance with an application of the present invention, an inventive concept including:

1. Apparatus for use with a sample suspected of containing an analyte, the apparatus comprising:

a test cartridge, comprising:

a casing that defines an internal space;

a membrane having a thickness of 0.1 nm-1 micron, the membrane disposed inside the casing, separating the internal space into a sample chamber and a second chamber, and fluidically and electrically isolating the second chamber from the sample chamber, and the casing shaped to define a port via which the sample is introducible into the sample chamber, a first electrode, disposed within the sample chamber;

a first cartridge-terminal, electrically connected to the first electrode, and accessible from outside of the cartridge;

a second electrode, disposed within the second chamber;
a second cartridge-terminal, electrically connected to the second electrode, and accessible from outside of the cartridge; and
a device for use with the test cartridge, the device comprising:
a dock, comprising a first dock-terminal and a second dock-terminal, and configured to receive the cartridge such that docking of the cartridge with the dock places the first and second cartridge-terminals in electrical contact with the first and second dock-terminals; and
circuitry, electrically connected to the cartridge-terminals, wherein the circuitry is configured to perform, while the cartridge remains docked with the dock:
(a) a nanoporation subroutine, in which the circuitry:
(i) applies nanoporation energy to the membrane, the nanoporation energy configured to ablate a nanopore in the membrane, and
(ii) monitors conduction of a pore-detection current between the first and second electrodes, and
(iii) ends the nanoporation subroutine upon detecting that the pore-detection current exceeds a threshold amplitude, the threshold amplitude being indicative of successful formation of a nanopore, and
(b) subsequently, an assay subroutine, in which the circuitry:
(i) applies an assay voltage between the first and second electrodes, the assay voltage having a magnitude of 0.01-5 V, and
(ii) while driving the assay voltage, simultaneously monitors electrical conduction between at least two of the dock-terminals.

2. The apparatus according to inventive concept 1, wherein the membrane is a solid-state membrane.

3. The apparatus according to inventive concept 1, wherein the membrane is a biological membrane.

4. The apparatus according to inventive concept 1, wherein the membrane is a block copolymer membrane.

5. The apparatus according to inventive concept 1, wherein the cartridge comprises a positive-control moiety having a known concentration, disposed in the internal space, the positive-control moiety being a positive control for the analyte.

6. The apparatus according to inventive concept 1, wherein the circuitry is configured such that steps (i) and (ii) of the nanoporation subroutine are performed iteratively.

7. The apparatus according to inventive concept 1, wherein the circuitry is configured such that steps (i) and (ii) of the nanoporation subroutine are performed simultaneously.

8. The apparatus according to inventive concept 1, wherein the circuitry is configured to apply a pore-detection voltage between the first and second electrodes during the nanoporation subroutine, the pore-detection current resulting from the application of the pore-detection voltage.

9. The apparatus according to inventive concept 1, wherein the nanoporation energy is a nanoporation voltage, the circuitry being configured to apply the nanoporation voltage between the first and second electrodes during the nanoporation subroutine, the pore-detection current resulting from the application of the nanoporation voltage.

10. The apparatus according to any one of inventive concepts 1-9, wherein the circuitry is configured to perform, prior to performing the nanoporation subroutine and the assay subroutine, a verification step during which the circuitry verifies an attribute of the cartridge.

11. The apparatus according to inventive concept 10, wherein the circuitry is configured to require that the attribute be successfully verified between (i) docking of the cartridge with the dock, and (ii) performing the nanoporation subroutine.

12. The apparatus according to inventive concept 11, wherein the circuitry is configured:
to detect undocking of the cartridge from the dock, and
to require, if the cartridge (i) becomes undocked from the dock after the attribute has been successfully verified, and (ii) is subsequently re-docked with the dock, that the verification step be re-performed between (i) the re-docking and (ii) performing the nanoporation subroutine and the assay subroutine.

13. The apparatus according to inventive concept 10, wherein the attribute is an absence of nanopores in the membrane, and the circuitry is configured to perform the verification step during which the circuitry verifies an absence of nanopores in the membrane.

14. The apparatus according to inventive concept 10, wherein the circuitry is configured to perform the verification step by monitoring conduction between the first and second electrodes.

15. The apparatus according to inventive concept 14, wherein the circuitry is configured to perform the verification step by applying a pore-detection voltage between the electrodes, and to monitor conduction, between the first and second electrodes, of a pore-detection current resulting from the pore-detection voltage.

16. The apparatus according to any one of inventive concepts 1-9, further comprising a user interface, wherein the circuitry is configured to determine a concentration of the analyte in the sample by analyzing data indicative of the electrical conduction monitored during the assay subroutine, and to responsively drive the user interface to display information indicative of the concentration of the analyte.

17. The apparatus according to inventive concept 16, wherein the circuitry is configured to display the information qualitatively.

18. The apparatus according to inventive concept 16, wherein the circuitry is configured to display the information quantitatively.

19. The apparatus according to inventive concept 16, wherein the user interface is a component of the device.

20. The apparatus according to inventive concept 16, wherein the user interface comprises a display.

21. The apparatus according to inventive concept 16, wherein the device comprises a computer interface, and the circuitry is configured to output the data to the user interface via the computer interface, the user interface being provided by software on a general-purpose computer.

22. The apparatus according to any one of inventive concepts 1-9, wherein the circuitry is further configured to perform, while the cartridge remains docked with the dock, a positive-control subroutine in which the circuitry:
(i) applies the assay voltage between the first and second electrodes, and
(ii) while driving the assay voltage, simultaneously monitors electrical conduction between at least two of the dock-terminals.

23. The apparatus according to inventive concept 22, wherein the cartridge comprises a positive-control moiety having a known concentration, disposed in the internal space, the positive-control moiety being a positive control for the analyte.

24. The apparatus according to inventive concept 22, wherein the circuitry is configured to determine a concentration of the analyte in the sample by analyzing (i) data indicative of the electrical conduction monitored during the assay subroutine, and (ii) data indicative of the electrical conduction monitored during the positive-control subroutine.

25. The apparatus according to any one of inventive concepts 1-9, wherein the nanoporation energy is a nanoporation voltage, the circuitry being configured to apply the nanoporation voltage between the first and second electrodes.

26. The apparatus according to inventive concept 25, wherein the circuitry is configured to apply the nanoporation voltage at a magnitude of 0.01-100 V.

27. The apparatus according to any one of inventive concepts 1-9, wherein the nanoporation energy is electromagnetic radiation energy, the circuitry being configured to apply the electromagnetic radiation energy to the membrane.

28. The apparatus according to inventive concept 27, wherein the device comprises an electromagnetic radiation source, the cartridge comprises an optical fiber, and the circuitry is configured to apply the electromagnetic radiation energy by driving the electromagnetic radiation source to radiate the electromagnetic radiation energy through the optical fiber.

29. The apparatus according to any one of inventive concepts 1-9, wherein the nanoporation energy is acoustic energy, the circuitry being configured to apply the acoustic energy to the membrane.

30. The apparatus according to inventive concept 29, wherein the device comprises an acoustic energy source, and the circuitry is configured to apply the acoustic energy by driving the acoustic energy source.

31. The apparatus according to inventive concept 29, wherein the acoustic energy is ultrasound energy, the circuitry being configured to apply the ultrasound energy to the membrane.

32. The apparatus according to any one of inventive concepts 1-9, wherein the cartridge further comprises a protective film coating a surface of the membrane, the film shaped to define an aperture through the film such that a target region of the surface is exposed through the aperture, the protective film configured to insulate the membrane from the nanoporation energy except for at the aperture, thereby biasing formation of the nanopore to the target region.

33. The apparatus according to inventive concept 32, wherein the film is an electrically-insulating film.

34. The apparatus according to inventive concept 32, wherein the film has a thickness of 1 nm-10 microns.

35. The apparatus according to inventive concept 32, wherein a sample-side of the membrane faces the sample chamber, and a second-side of the membrane faces the second chamber, and wherein the film is disposed on the sample-side of the membrane.

36. The apparatus according to inventive concept 32, wherein a sample-side of the membrane faces the sample chamber, and a second-side of the membrane faces the second chamber, and wherein the film is disposed on the second-side of the membrane.

37. The apparatus according to inventive concept 32, wherein the film is shaped such that the aperture has a width of 0.001-1 micron.

38. The apparatus according to inventive concept 32, wherein the film is shaped such that the aperture has a width of 0.1-10 microns.

39. The apparatus according to inventive concept 32, wherein the cartridge further comprises a support on which the membrane is disposed, the support supporting the membrane and being shaped to define a window through which a zone of the membrane is exposed.

40. The apparatus according to inventive concept 39, wherein a width of the aperture is smaller than a width of the window.

41. The apparatus according to inventive concept 39, wherein the support is shaped such that the window has a width of 1-500 microns.

42. The apparatus according to inventive concept 39, wherein:
the surface is a first surface of the membrane on a first side of the membrane, and the film coats the first surface of the membrane such that the target region is on the first surface of the membrane, and
the support is disposed against a second surface of the membrane on a second side of the membrane that is opposite the first side of the membrane, such that the zone of the membrane is on the second side of the membrane.

43. The apparatus according to inventive concept 42, wherein the aperture and the window are positioned such that the target region is aligned with the zone.

44. The apparatus according to inventive concept 39, wherein:
the surface is a first surface of the membrane on a first side of the membrane,
the support is disposed against the first side of the membrane, and
the film coats the first surface of the membrane within the zone, such that the target region is on the first surface of the membrane within the zone.

45. The apparatus according to inventive concept 39, wherein the membrane is a silicon-based membrane, and the support comprises silicon.

46. The apparatus according to inventive concept 32, wherein the membrane is a silicon-based membrane.

47. The apparatus according to inventive concept 32, wherein the membrane is a 2D-material-based membrane.

48. The apparatus according to inventive concept 32, wherein the aperture is exactly one aperture, and the film is shaped to define the exactly one aperture.

49. The apparatus according to inventive concept 32, wherein chemistry of the surface at the target region is modified by a chemical moiety that is bound to the surface only at the target region.

There is further provided, in accordance with an application of the present invention, an inventive concept including:

50. Apparatus for use with a test cartridge, comprising:
a dock, configured to receive the test cartridge;
a plurality of dock-terminals, positioned with respect to the dock so as to become electrically contacted with the test cartridge upon the dock receiving the test cartridge; and
circuitry, configured to perform:
(a) a nanoporation subroutine, in which the circuitry iteratively:
(i) applies a nanoporation voltage between at least two of the dock-terminals, the nanoporation voltage having a magnitude of 1-100 V, and
(ii) applies a pore-detection voltage between at least two of the dock-terminals, and detects conduction of a pore-detection current resulting from the applied pore-detection voltage, the pore-detection voltage having a magnitude of 10-900 mV,
until the detected conduction is above a threshold amplitude, and
(b) an assay subroutine, in which the circuitry:
(i) applies a translocation voltage between at least two of the dock-terminals, the translocation voltage having a magnitude of 0.01-5 V, and
(ii) while driving the translocation voltage, simultaneously monitors electrical conduction between at least two of the dock-terminals.

There is further provided, in accordance with an application of the present invention, an inventive concept including:

51. Apparatus, comprising:
a membrane having a thickness of 0.1 nm-1 micron; and
an electrically-insulating film having a thickness of 1 nm-10 microns, coating a surface of the membrane, and shaped to define an aperture through the film, such that a target region of the surface is exposed through the aperture.

52. The apparatus according to inventive concept 51, wherein the membrane is a solid-state membrane.

53. The apparatus according to inventive concept 51, wherein the membrane is a biological membrane.

54. The apparatus according to inventive concept 51, wherein the membrane is a block copolymer membrane.

55. The apparatus according to inventive concept 51, wherein the film is shaped such that the aperture has a width of 0.001-1 micron.

56. The apparatus according to inventive concept 51, wherein the film is shaped such that the aperture has a width of 0.1-10 microns.

57. The apparatus according to inventive concept 51, further comprising a support on which the membrane is disposed, the support supporting the membrane and being shaped to define a window through which a zone of the membrane is exposed, wherein the membrane is a silicon-based membrane, and wherein the support comprises silicon.

58. The apparatus according to inventive concept 51, wherein the membrane is a silicon-based membrane.

59. The apparatus according to inventive concept 51, wherein the membrane is a 2D-material-based membrane.

60. The apparatus according to inventive concept 51, wherein the aperture is exactly one aperture, and the film is shaped to define the exactly one aperture.

61. The apparatus according to any one of inventive concepts 51-60, further comprising:
a casing that defines an internal space, the membrane disposed inside the casing, and separating the internal space into a sample chamber and a second chamber, the membrane fluidically and electrically isolating the second chamber from the sample chamber, and the casing shaped to define a port via which a sample is introducible into the sample chamber,
a first electrode, disposed within the sample chamber;
a first cartridge-terminal, electrically connected to the first electrode, and accessible from outside of the cartridge;
a second electrode, disposed within the second chamber; and
a second cartridge-terminal, electrically connected to the second electrode, and accessible from outside of the cartridge.

62. The apparatus according to inventive concept 61, wherein a sample-side of the membrane faces the sample chamber, and a second-side of the membrane faces the second chamber, and wherein the film is disposed on the sample-side of the membrane.

63. The apparatus according to inventive concept 61, wherein a sample-side of the membrane faces the sample chamber, and a second-side of the membrane faces the second chamber, and wherein the film is disposed on the second-side of the membrane.

64. The apparatus according to any one of inventive concepts 51-60, wherein the apparatus further comprises a support on which the membrane is disposed, the support supporting the membrane and being shaped to define a window through which a zone of the membrane is exposed.

65. The apparatus according to inventive concept 64, wherein a width of the aperture is smaller than a width of the window.

66. The apparatus according to inventive concept 64, wherein the support is shaped such that the window has a width of 1-500 microns.

67. The apparatus according to inventive concept 64, wherein:
the surface is a first surface of the membrane on a first side of the membrane, and the film coats the first surface of the membrane such that the target region is on the first surface of the membrane, and
the support is disposed against a second surface of the membrane on a second side of the membrane that is opposite the first side of the membrane, such that the zone of the membrane is on the second side of the membrane.

68. The apparatus according to inventive concept 67, wherein the aperture and the window are positioned such that the target region is aligned with the zone.

69. The apparatus according to inventive concept 64, wherein:
the surface is a first surface of the membrane on a first side of the membrane,
the support is disposed against the first side of the membrane, and
the film coats the first surface of the membrane within the zone, such that the target region is on the first surface of the membrane within the zone.

70. The apparatus according to any one of inventive concepts 51-60, wherein chemistry of the surface at the target region is modified by a chemical moiety that is bound to the surface only at the target region.

71. The apparatus according to inventive concept 70, wherein the chemical moiety is silane.

72. The apparatus according to inventive concept 70, wherein the chemical moiety is a thiol.

73. The apparatus according to inventive concept 70, wherein the chemical moiety is an amino acid.

74. The apparatus according to inventive concept 70, wherein the chemical moiety is a carboxylic acid.

75. The apparatus according to inventive concept 70, wherein the chemical moiety is an azide.

76. The apparatus according to inventive concept 70, wherein the chemical moiety is an amide.

77. The apparatus according to inventive concept 70, wherein the chemical moiety is a sugar.

78. The apparatus according to inventive concept 70, wherein the chemical moiety is an immunoglobulin.

79. The apparatus according to inventive concept 70, wherein the chemical moiety is a nucleic acid.

80. The apparatus according to inventive concept 79, wherein the chemical moiety is an oligonucleotide.

81. The apparatus according to inventive concept 80, wherein the chemical moiety is an aptamer.

82. The apparatus according to inventive concept 70, wherein the chemical moiety is a peptide nucleic acid.

83. The apparatus according to inventive concept 70, wherein the chemistry of the surface is modified to have increased hydrophilicity.
84. The apparatus according to inventive concept 70, wherein the chemistry of the surface is modified to have decreased hydrophilicity.
85. The apparatus according to inventive concept 70, wherein the chemistry of the surface is modified to have an increased affinity for immunoglobulins.
86. The apparatus according to inventive concept 70, wherein the chemistry of the surface is modified to have an increased affinity for nucleic acids.
87. The apparatus according to inventive concept 70, wherein the chemistry of the surface is modified to have an increased affinity for nucleic acids having a particular sequence.
88. The apparatus according to inventive concept 70, wherein the chemistry of the surface is modified to have an increased affinity for sugars.
89. The apparatus according to inventive concept 70, wherein the chemistry of the surface is modified to have an increased affinity for polypeptides.
90. The apparatus according to inventive concept 70, wherein the chemistry of the surface is modified to have an increased affinity for aldehydes.
91. The apparatus according to inventive concept 70, wherein the chemistry of the surface is modified to have an increased affinity for ketones.
92. The apparatus according to inventive concept 70, wherein the chemistry of the surface is modified to have an increased affinity for alkynes.
93. The apparatus according to inventive concept 70, wherein the chemistry of the surface is modified to have an increased affinity for azides.
94. The apparatus according to inventive concept 70, wherein the chemistry of the surface is modified to have an increased affinity for esters.
95. The apparatus according to inventive concept 70, wherein the chemistry of the surface is modified to have an increased affinity for carboxyls.
96. The apparatus according to inventive concept 70, wherein the chemistry of the surface is modified to have an increased affinity for boric acid.
97. The apparatus according to inventive concept 70, wherein the chemistry of the surface is modified to have an increased affinity for methoxyethene.
98. The apparatus according to inventive concept 70, wherein the chemistry of the surface is modified to have an increased affinity for epoxies.

There is further provided, in accordance with an application of the present invention, an inventive concept including:
99. Apparatus, comprising:
a membrane having a thickness of 0.1 nm-1 micron, the membrane being susceptible to ablation by application of an energy; and
a casing that defines an internal space, the membrane disposed inside the casing, and separating the internal space into a sample chamber and a second chamber, the membrane fluidically and electrically isolating the second chamber from the sample chamber, and the casing shaped to define a port via which a sample is introducible into the sample chamber,
a first electrode, disposed within the sample chamber;
a first cartridge-terminal, electrically connected to the first electrode, and accessible from outside of the cartridge;
a second electrode, disposed within the second chamber;
a second cartridge-terminal, electrically connected to the second electrode, and accessible from outside of the cartridge; and
a protective film having a thickness of 1 nm-10 microns, coating a surface of the membrane, shaped to define exactly one aperture through the film such that a target region of the surface is exposed through the aperture, and configured to protect the membrane from the energy except for at the aperture.
100. The apparatus according to inventive concept 99, wherein the membrane is a solid-state membrane.
101. The apparatus according to inventive concept 99, wherein the membrane is a biological membrane.
102. The apparatus according to inventive concept 99, wherein the membrane is a block copolymer membrane.
103. The apparatus according to inventive concept 99, wherein a sample-side of the membrane faces the sample chamber, and a second-side of the membrane faces the second chamber, and wherein the film is disposed on the sample-side of the membrane.
104. The apparatus according to inventive concept 99, wherein a sample-side of the membrane faces the sample chamber, and a second-side of the membrane faces the second chamber, and wherein the film is disposed on the second-side of the membrane.
105. The apparatus according to inventive concept 99, wherein the film is shaped such that the aperture has a width of 0.001-1 micron.
106. The apparatus according to inventive concept 99, wherein the film is shaped such that the aperture has a width of 0.1-10 microns.
107. The apparatus according to inventive concept 99, further comprising a support on which the membrane is disposed, the support supporting the membrane and being shaped to define a window through which a zone of the membrane is exposed, wherein the membrane is a silicon-based membrane, and the support comprises silicon.
108. The apparatus according to inventive concept 99, wherein the membrane is a silicon-based membrane.
109. The apparatus according to inventive concept 99, wherein the membrane is a 2D-material-based membrane.
110. The apparatus according to any one of inventive concepts 99-109, wherein the energy is electrical energy, and the film is an electrically-insulating film.
111. The apparatus according to inventive concept 110, wherein the first electrode, the first cartridge-terminal, the second electrode, and the second cartridge-terminal are configured to facilitate ablation of the membrane at the aperture via application of the electrical energy.
112. The apparatus according to any one of inventive concepts 99-109, wherein the apparatus further comprises a support on which the membrane is disposed, the support supporting the membrane and being shaped to define a window through which a zone of the membrane is exposed.
113. The apparatus according to inventive concept 112, wherein a width of the aperture is smaller than a width of the window.
114. The apparatus according to inventive concept 112, wherein the support is shaped such that the window has a width of 1-500 microns.
115. The apparatus according to inventive concept 112, wherein:
the surface is a first surface of the membrane on a first side of the membrane, and the film coats the first surface of the membrane such that the target region is on the first surface of the membrane, and the support is disposed against a second surface of the membrane on a second side of the membrane that is opposite the first side of the membrane, such that the zone of the membrane is on the second side of the membrane.
116. The apparatus according to inventive concept 115, wherein the aperture and the window are positioned such that the target region is aligned with the zone.
117. The apparatus according to inventive concept 112, wherein:
the surface is a first surface of the membrane on a first side of the membrane,
the support is disposed against the first side of the membrane, and
the film coats the first surface of the membrane within the zone, such that the target region is on the first surface of the membrane within the zone.
118. The apparatus according to any one of inventive concepts 99-109, wherein chemistry of the surface at the target region is modified by a chemical moiety that is bound to the surface only at the target region.
119. The apparatus according to inventive concept 118, wherein the chemical moiety is silane.
120. The apparatus according to inventive concept 118, wherein the chemical moiety is a thiol.
121. The apparatus according to inventive concept 118, wherein the chemical moiety is an amino acid.
122. The apparatus according to inventive concept 118, wherein the chemical moiety is a carboxylic acid.
123. The apparatus according to inventive concept 118, wherein the chemical moiety is an azide.
124. The apparatus according to inventive concept 118, wherein the chemical moiety is an amide.
125. The apparatus according to inventive concept 118, wherein the chemical moiety is a sugar.
126. The apparatus according to inventive concept 118, wherein the chemical moiety is an immunoglobulin.
127. The apparatus according to inventive concept 118, wherein the chemical moiety is a nucleic acid.
128. The apparatus according to inventive concept 127, wherein the chemical moiety is an oligonucleotide.
129. The apparatus according to inventive concept 128, wherein the chemical moiety is an aptamer.
130. The apparatus according to inventive concept 118, wherein the chemical moiety is a peptide nucleic acid.
131. The apparatus according to inventive concept 118, wherein the chemistry of the surface is modified to have increased hydrophilicity.
132. The apparatus according to inventive concept 118, wherein the chemistry of the surface is modified to have decreased hydrophilicity.
133. The apparatus according to inventive concept 118, wherein the chemistry of the surface is modified to have an increased affinity for immunoglobulins.
134. The apparatus according to inventive concept 118, wherein the chemistry of the surface is modified to have an increased affinity for nucleic acids.
135. The apparatus according to inventive concept 118, wherein the chemistry of the surface is modified to have an increased affinity for nucleic acids having a particular sequence.
136. The apparatus according to inventive concept 118, wherein the chemistry of the surface is modified to have an increased affinity for sugars.
137. The apparatus according to inventive concept 118, wherein the chemistry of the surface is modified to have an increased affinity for polypeptides.
138. The apparatus according to inventive concept 118, wherein the chemistry of the surface is modified to have an increased affinity for aldehydes.
139. The apparatus according to inventive concept 118, wherein the chemistry of the surface is modified to have an increased affinity for ketones.
140. The apparatus according to inventive concept 118, wherein the chemistry of the surface is modified to have an increased affinity for alkynes.
141. The apparatus according to inventive concept 118, wherein the chemistry of the surface is modified to have an increased affinity for azides.
142. The apparatus according to inventive concept 118, wherein the chemistry of the surface is modified to have an increased affinity for esters.
143. The apparatus according to inventive concept 118, wherein the chemistry of the surface is modified to have an increased affinity for carboxyls.
144. The apparatus according to inventive concept 118, wherein the chemistry of the surface is modified to have an increased affinity for boric acid.
145. The apparatus according to inventive concept 118, wherein the chemistry of the surface is modified to have an increased affinity for methoxyethene.
146. The apparatus according to inventive concept 118, wherein the chemistry of the surface is modified to have an increased affinity for epoxies.
There is further provided, in accordance with an application of the present invention, an inventive concept including:
147. Apparatus for use with a sample, the apparatus comprising a test cartridge that comprises:
a casing that defines an internal space;
a membrane that:
has a thickness of less than 1 micron,
is disposed inside the casing, and
separates the internal space into a sample chamber and a second chamber, fluidically and electrically isolating the second chamber from the sample chamber, the casing being shaped to define a port via which the sample is introducible into the sample chamber,
a seal, sealing the port;
a first electrode, disposed within the sample chamber;
a first cartridge-terminal, electrically connected to the first electrode, and accessible from outside of the cartridge;
a second electrode, disposed within the second chamber;
a second cartridge-terminal, electrically connected to the second electrode, and accessible from outside of the cartridge,
wherein:
in the presence of the seal, the sample chamber and the second chamber are each hermetically sealed, and
in the absence of the seal, the sample chamber is fluidically accessible from outside of the casing via the port, but the second chamber remains hermetically sealed.
148. The apparatus according to inventive concept 147, wherein the membrane is a solid-state membrane.
149. The apparatus according to inventive concept 147, wherein the membrane is a biological membrane.
150. The apparatus according to inventive concept 147, wherein the membrane is a block copolymer membrane.
151. The apparatus according to inventive concept 147, further comprising a sealed packaging in which the test cartridge is disposed.
152. The apparatus according to inventive concept 147, wherein a sample-side of the membrane faces the sample chamber, a second-side of the membrane faces the second chamber, and surface chemistry of the membrane is modified by a chemical moiety that is bound to the membrane only on the second side.
153. The apparatus according to any one of inventive concepts 147-152, further comprising a film having a thickness of 1 nm-10 microns, coating a surface of the membrane, and shaped to define an aperture through the film, such that a target region of the surface is exposed through the aperture.
154. The apparatus according to inventive concept 153, wherein the film is an electrically-insulating film.
155. The apparatus according to inventive concept 153, wherein the film is disposed on a side of the membrane that faces the sample chamber.
156. The apparatus according to inventive concept 153, wherein the film is disposed on a side of the membrane that faces the second chamber.
157. The apparatus according to inventive concept 153, wherein chemistry of the surface at the target region is modified by a chemical moiety that is bound to the surface only at the target region.

There is further provided, in accordance with an application of the present invention, an inventive concept including:
158. A method for detecting an analyte within a sample, the method comprising:
docking a test cartridge with a dock of a device such that, while the cartridge is docked with the device, (i) at least one first cartridge-terminal of the cartridge is in electrical contact with at least one first dock-terminal of the device, and (ii) at least one second cartridge-terminal of the cartridge is in electrical contact with at least one second dock-terminal of the device, the test cartridge including:
a casing that defines an internal space,
a membrane that separates the internal space into a sample chamber and a second chamber, fluidically and electrically isolating the second chamber from the sample chamber,
at least one first electrode, disposed within the sample chamber, and electrically connected to the at least one first cartridge-terminal, and
at least one second electrode, disposed within the second chamber, and electrically connected to the at least one second cartridge-terminal;
loading the sample into the sample chamber via a sample port that is defined by the casing; and
while the cartridge remains docked with the device, activating the device to, via the electrical contact between (i) the at least one first dock-terminal and the at least one first cartridge-terminal, and (ii) the at least one second dock-terminal and the at least one second cartridge-terminal:
form a nanopore in the membrane by applying a nanoporation energy to the membrane, and
subsequently:
apply an assay voltage between (i) the at least one first electrode and (ii) the at least one second electrode, the assay voltage having a magnitude of 0.01-5 V, and
detect translocation of the analyte through the nanopore by detecting changes in electrical conduction between the electrodes via the nanopore.

There is further provided, in accordance with an application of the present invention, an inventive concept including:
159. Apparatus, comprising:
a dock;
a first dock-terminal positioned at the dock and a second dock-terminal positioned at the dock; and
circuitry, configured to:
perform a subroutine in which the circuitry automatically:
applies a voltage between the first and second dock-terminals, periodically changes a magnitude of the voltage, and
monitors conduction of a current between the first and second dock-terminals, and
automatically stop the subroutine in response to detecting that an amplitude of the current exceeds a threshold amplitude,
wherein the circuitry is provided to apply a buffer period after changing the magnitude of the voltage, and to ignore the current during the buffer period, such that the circuitry does not automatically stop the subroutine in response to the amplitude exceeding the threshold amplitude during the buffer period.
160. The apparatus according to inventive concept 159, further comprising a test cartridge configured to be docked to the dock, the test cartridge comprising:
a membrane having a thickness of 0.1 nm-1 micron; and
a casing that defines an internal space, the membrane disposed inside the casing, and separating the internal space into a sample chamber and a second chamber, the membrane fluidically and electrically isolating the second chamber from the sample chamber, and the casing shaped to define a port via which a sample is introducible into the sample chamber,
a first electrode, disposed within the sample chamber;
a second electrode, disposed within the second chamber;
a first cartridge-terminal, electrically connected to the first electrode; and,
a second cartridge-terminal, electrically connected to the second electrode, wherein:
the first and second cartridge-terminals are accessible from outside of the cartridge such that docking of the test cartridge to the dock places the first and second cartridge-terminals in electrical contact with the first and second dock-terminals, and
while the cartridge is docked with the dock:
the circuitry is configured to create a nanopore in the membrane by applying the voltage, and
the circuitry is configured to detect the nanopore in the membrane by monitoring the conduction.

There is further provided, in accordance with an application of the present invention, an inventive concept including:
161. Apparatus for facilitating nanopore-based detection of an analyte in a sample, the apparatus comprising:
a casing that defines an internal space;
a membrane having a thickness of 0.1 nm-1 micron, the membrane disposed inside the casing, and separating the internal space into a sample chamber and a second chamber, and the casing shaped to define a port via which the sample is introducible into the sample chamber,
a first electrode, disposed within the sample chamber;
a first cartridge-terminal, electrically connected to the first electrode, and accessible from outside of the cartridge;
a second electrode, disposed within the second chamber;
a second cartridge-terminal, electrically connected to the second electrode, and accessible from outside of the cartridge; and
a positive-control moiety having a known concentration, disposed in the internal space, the positive-control moiety being a positive control for the analyte.
162. The apparatus according to inventive concept 161, wherein the membrane is a solid-state membrane.
163. The apparatus according to inventive concept 161, wherein the membrane is a biological membrane.
164. The apparatus according to inventive concept 161, wherein the membrane is a block copolymer membrane.

165. The apparatus according to inventive concept 161, wherein the positive-control moiety is disposed in the sample chamber.
166. The apparatus according to inventive concept 161, wherein the positive-control moiety is disposed in the second chamber.
167. The apparatus according to inventive concept 161, wherein the membrane fluidically and electrically isolates the second chamber from the sample chamber.
168. The apparatus according to inventive concept 161, wherein the membrane is shaped to define a nanopore between the sample chamber and the second chamber, and dimensioned to facilitate translocation of the positive-control moiety through the nanopore.
169. The apparatus according to any one of inventive concepts 161-168, wherein the apparatus comprises a kit that comprises:
a test cartridge that comprises the casing, the membrane, the first and second electrodes, the first and second cartridge-terminals, and the positive-control moiety; and
at least one nucleic acid primer appropriate for amplification of the analyte.
170. The apparatus according to inventive concept 169, wherein the kit further comprises a polymerase.
171. The apparatus according to any one of inventive concepts 161-168, further comprising at least one nucleic acid primer appropriate for amplification of the analyte, the at least one nucleic acid primer disposed in the internal space.
172. The apparatus according to inventive concept 171, wherein the at least one nucleic acid primer is disposed in the sample chamber.
173. The apparatus according to inventive concept 171, further comprising a polymerase disposed in the internal space.
174. The apparatus according to inventive concept 173, wherein the at least one polymerase is disposed in the sample chamber.

The present invention will be more fully understood from the following detailed description of applications thereof, taken together with the drawings, in which:

BRIEF DESCRIPTION OF THE DRAWINGS

FIGS. 8A-B are schematic illustrations that show a site of nanoporation of a membrane of a test cartridge before and after formation of a nanopore, in accordance with some such applications of the invention;

FIGS. 9A-B are schematic illustrations that show a site of nanoporation of a membrane of a test cartridge before and after formation of a nanopore, in accordance with some such applications of the invention;

FIGS. 10A-B are schematic illustrations showing surface modification of a membrane of a test cartridge, in accordance with some applications of the invention;

FIGS. 11A-B are schematic illustrations showing surface modification of a membrane of a test cartridge, in accordance with some applications of the invention;

FIGS. 12A-C are schematic illustrations showing surface modification of a membrane of a test cartridge, in accordance with some applications of the invention;

DETAILED DESCRIPTION OF EMBODIMENTS

Figure 1:
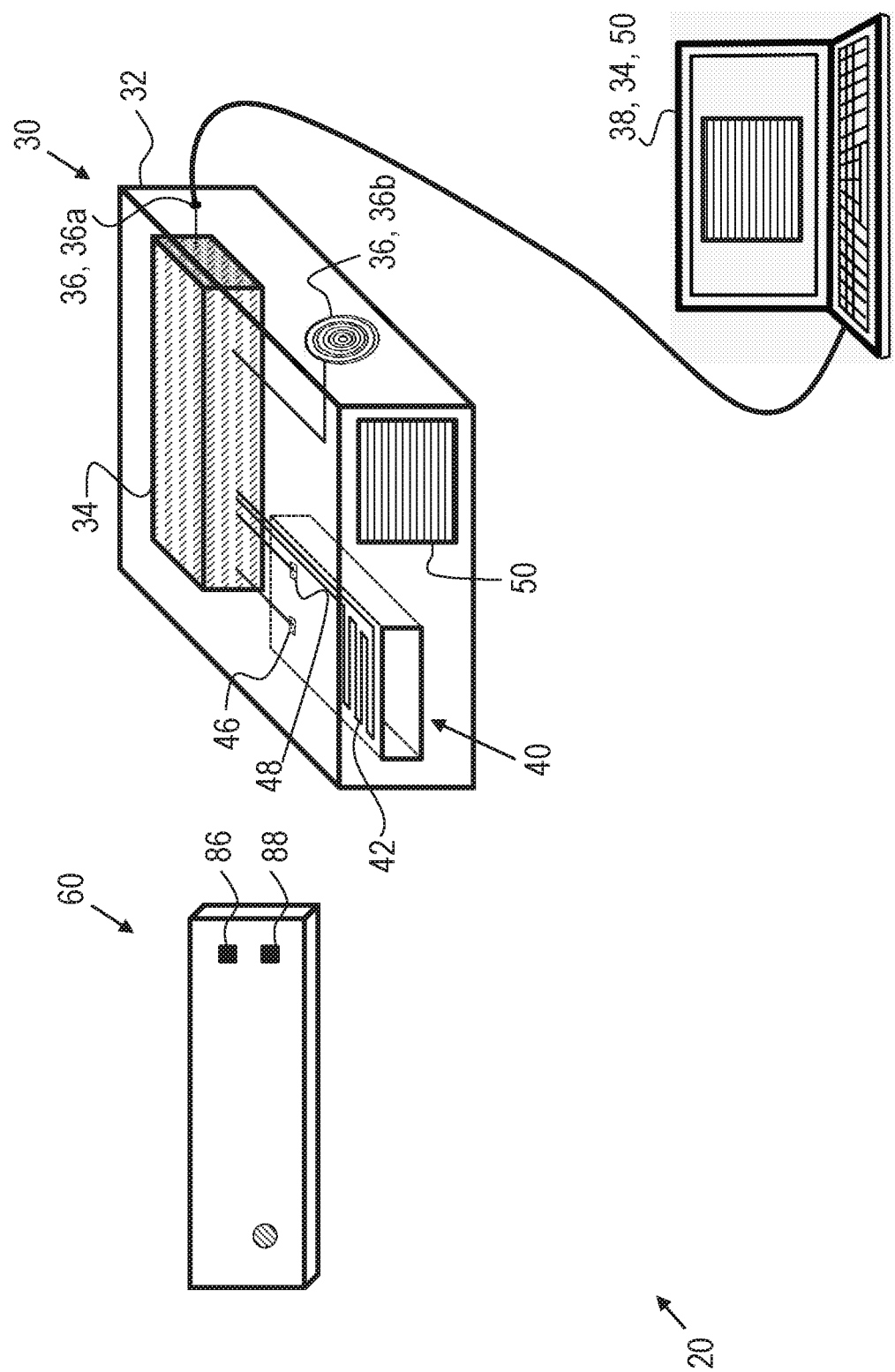
FIG. 1 is a schematic illustration of a system that comprises a device and a test cartridge, in accordance with some applications of the invention.

Reference is made to FIG. 1, which is a schematic illustration of a system 20, which comprises a device 30 and a test cartridge 60, in accordance with some applications of the invention. System 20 is typically used for nanopore-based assays of samples, e.g., for detecting analytes such as polymers (e.g., nucleic acids, polypeptides (e.g., proteins), polysaccharides), small molecules, and/or moieties (e.g., tags) bound thereto.

Figure 2:
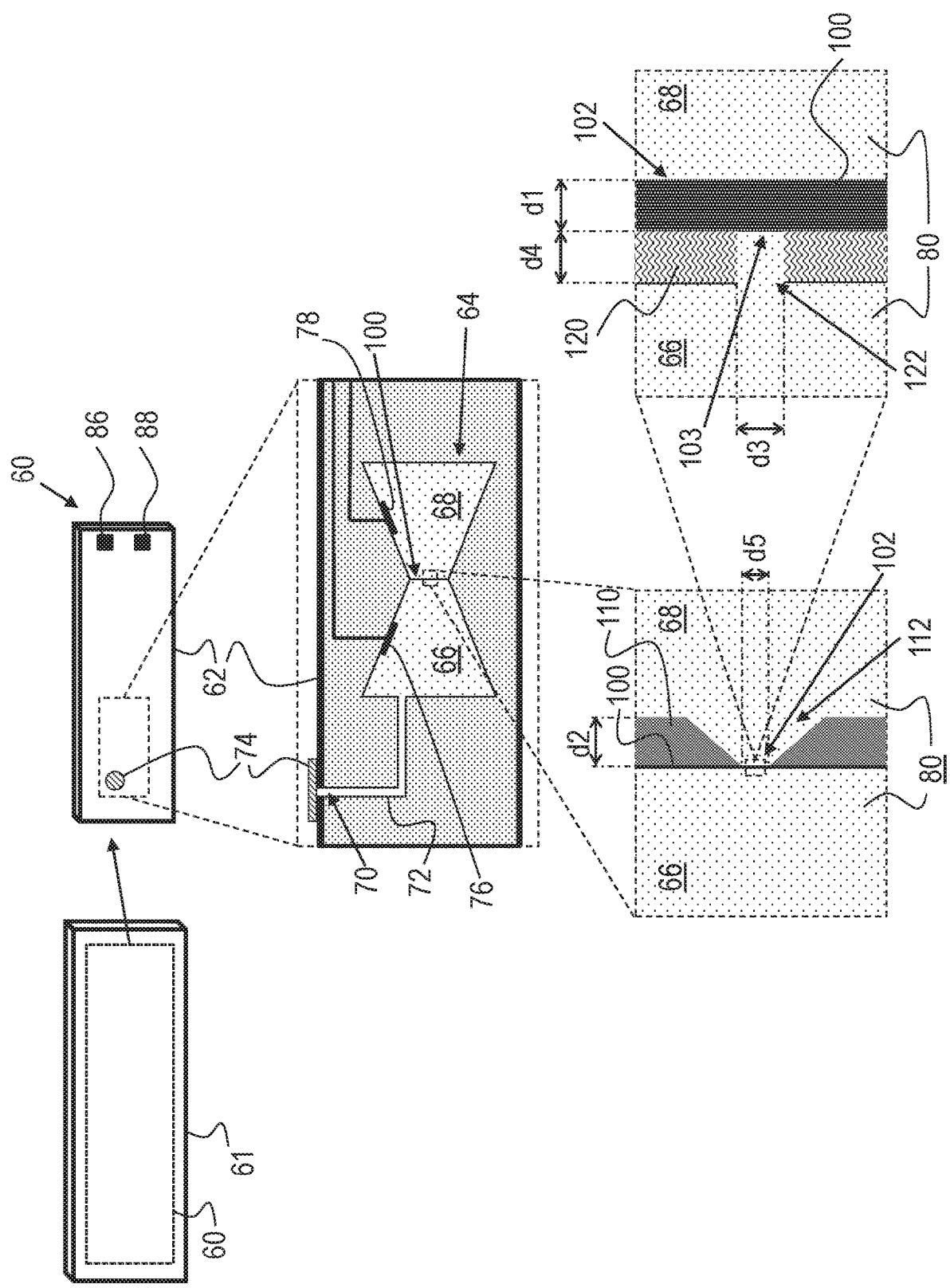
FIG. 2 is a schematic illustration of the cartridge, in accordance with some applications of the invention.

Reference is also made to FIG. 2, which is a schematic illustration of cartridge 60, in accordance with some applications of the invention. Cartridge 60 comprises a casing 62 that defines an internal space 64, and a membrane 100 that separates the internal space into a sample chamber 66 and a second chamber 68. Typically, membrane 100 fluidically and electrically isolates the second chamber from the sample chamber. Membrane 100 is typically a solid-state membrane. For some applications membrane 100 is a biological membrane. For some applications membrane 100 is a block copolymer membrane. Membrane 100 typically has a thickness $d1$ of less than 1 micron and/or greater than 0.1 nm (e.g., 0.1-500 nm, e.g., 0.1-100 nm, e.g., 1-50 nm, such as 5-30 nm).

Casing 62 is shaped to define a port 70, via which the sample to be tested is introducible into sample chamber 66. For example, and as shown, port 70 may be in fluid communication with chamber 66 via a channel (e.g., a microfluidic channel) 72. The fluidic isolation provided by membrane 100 is typically such that, prior to nanoporation (described hereinbelow), the sample cannot translocate from the sample chamber into the second chamber.

Cartridge 60 is typically provided with an electrically-conductive liquid 80 disposed in chambers 66 and 68. For some applications, liquid 80 is aqueous. For some applications, liquid 80 is organic. For some applications, liquid 80 is an ionic liquid. Membrane 100 typically fluidically and electrically isolates chamber 68 from chamber 66 despite the presence of liquid 80 in both chambers.

A first electrode 76 is disposed within sample chamber 66 (i.e., such that the electrode is in electrical contact with liquid 80), and is electrically connected to a first cartridge-terminal 86 (i.e., a terminal of cartridge 60) that is accessible from outside of cartridge 60. A second electrode 78 is disposed within second chamber 68 (i.e., such that the electrode is in electrical contact with liquid 80), and is electrically connected to a second cartridge-terminal 88 (i.e., a terminal of cartridge 60) that is accessible from outside of cartridge 60. It is to be noted that in this context, cartridge-terminals 86 and 88 being "accessible from outside" of cartridge 60 means that they are accessible to be placed in electrical contact with corresponding terminals of a complimentary device, such as device 30, e.g., as described hereinbelow. Therefore, the scope of the invention includes configurations of cartridge 60 in which the cartridge-terminals are disposed on an outer surface of casing 62 (e.g., in a straightforward manner) e.g., as shown, as well as configurations in which the cartridge-terminals are obscured by other elements of the cartridge, such as within a cavity or socket defined by the casing.

For some applications, liquid 80 in chamber 68 is identical to that in chamber 66. However, although reference numeral 80 is used to indicate the liquid in both chambers, for some applications the liquid in one of the chambers is different to that in the other. For example, the concentration of one or more electrolytes may be different in one chamber compared to in the other chamber. For some applications, in chamber 66 liquid 80 is an aqueous liquid, an organic liquid, or an ionic liquid, and the liquid in chamber 68 is a different one of these.

Cartridge 60 is typically provided with a seal 74 sealing the port. For some applications, and as shown, cartridge 60 is provided within a sealed packaging 61 (i.e., distinct from casing 62 and seal 74). In the presence of seal 74, sample chamber 66 and second chamber 68 are each hermetically sealed. In the absence of seal 74 (e.g., after the seal has been broken or removed), sample chamber 66 is fluidically accessible from outside of casing 62 via port 70, but second chamber 68 remains hermetically sealed, e.g., because of the presence of membrane 100. For some applications, seal 74 is a removable plug or covering. For some applications, seal 74 is frangible. For some applications, seal 74 is resealable. For some applications, seal 74 is configured to be pierced by a hollow needle. For some applications, seal 74 comprises a valve.

Device 30 comprises a housing 32, a dock 40, and a plurality of dock-terminals (i.e., terminals of the dock). The plurality of dock-terminals includes at least a first dock-terminal 46 and a second dock-terminal 48. Dock 40 is configured to receive cartridge 60, and the dock-terminals are positioned with respect to the dock so as to become electrically contacted with the test cartridge upon the dock receiving the test cartridge. For example, and as shown, dock 40 may be a socket defined by housing 32, and dock-terminals 46 and 48 may be disposed within the socket.

Device 30 further comprises circuitry 34, which is electrically connected to dock-terminals 46 and 48.

Device 30 is configured to facilitate or perform nanopore-based assays of a sample that is introduced into cartridge 60 via port 70, e.g., to detect and/or quantify an analyte in the sample. Device 30 is configured to do this by application of electrical voltage between electrodes 76 and 78 (and thereby across membrane 100), and detection of the resulting electrical current between the electrodes. This is performed while the electrodes are electrically connected to circuitry 34 via the electrical contact between the dock-terminals and the cartridge terminals, which is provided by the docking of the cartridge with dock 40. This assaying is described in further detail hereinbelow.

Unusually, cartridge 60 is typically provided with membrane 100 intact (i.e., without the membrane defining a nanopore therethrough) and the membrane thereby fluidically and electrically isolates second chamber 68 from sample chamber 66. In the absence of a nanopore, cartridge 60 is unsuitable for nanopore-based assays. For applications in which cartridge 60 is provided with membrane 100 intact, device 30 is typically further configured to create a nanopore 104 in membrane 100 via ablation. This nanoporation is also achieved by application of a voltage between electrodes 76 and 78 (and thereby across membrane 100). This is performed while the electrodes are electrically connected to circuitry 34 via the electrical contact between the dock-terminals and the cartridge terminals, which is provided by the docking of the cartridge with dock 40. This "nanoporation" is described in further detail hereinbelow.

Nanopore-based assays depend upon the quality of the nanopore(s) being used, e.g., having a desirable and reliable size and shape. It is hypothesized by the inventors that nanopores change (e.g., in dimension and/or quality) over time after their formation, and that it is therefore advantageous to perform nanopore-based assays as soon as possible after the nanopore has been formed. It is further hypothesized that movement and/or handling of membranes subsequently to nanopore formation is deleterious to the nanopore, and that it is therefore advantageous to perform nanopore-based assays without moving the membrane after nanopore formation.

Therefore, for applications in which cartridge 60 is provided with membrane 100 intact, device 30 (e.g., circuitry 34 thereof) is configured to perform (a) a nanoporation subroutine, and (b) an assay subroutine. These subroutines are described in more detail hereinbelow. For such applications, device 30 is typically configured to perform the nanoporation and assay subroutines while dock-terminals 46 and 48 remain in contact with cartridge-terminals 86 and 88 (i.e., without contact being broken).

Device 30 (e.g., circuitry 34 thereof) is configured to interface with a user. For some applications, device 30 comprises a user interface (UI) 50, such as a display, buttons, and/or a touchscreen. Alternatively or additionally, device 30 comprises a computer interface 36 such as a connector 36a (typically of an industry standard, such as USB) and/or a wireless transceiver 36b (typically of an industry standard, such as Bluetooth, NFC, or WiFi), and the device is configured to use the computer 38 with which it interfaces, as UI 50. For some applications, at least some of the functions of circuitry 34 are performed by computer 38, e.g., such that circuitry of the computer may serve as circuitry 34. For some applications, computer 38 is typically a general-purpose computer, and UI software is typically provided to provide the computer with the functionality of UI 50 and/or of circuitry 34. Computer 38 is shown as a laptop, but may be a different format of computer, such as, but not limited to, a desktop, tablet, or smartphone.

Membrane 100 is typically formed using techniques known in the art. For sonic applications, and as shown, membrane 100 is a silicon-based membrane, e.g., comprising silicon, silicon nitride, silicon dioxide, quartz, and/or glass. For such applications, and as shown, membrane 100 is typically supported by a support 110, on which the membrane is disposed. Support 110 is typically shaped as a slab. For silicon-based membranes support 110 typically comprises silicon (e.g., pure silicon). As is known in the art, support 110 is typically shaped to define a window 112 therethrough, exposing a relatively small zone 102 of membrane 100, within which a nanopore 104 will be formed. Support 110 thereby structurally supports membrane 100 over the majority of the surface area of the membrane, while providing a suitable zone 102 of the membrane for nanoporation. Window 112 has a width d5. The width d5 of window 112 is defined as the width of zone 102 that the window exposes, irrespective of whether the window has sloped sides (e.g., as shown) or straight sides. Support 110 typically has a thickness d2 of 1-500 microns (e.g., 10-400 microns, e.g., 100-400 microns, such as 200-300 microns). Width d5 of window 112 is typically 1-500 microns 2-100 microns, such as 5-50 microns).

Although support 110 is shown on the side of membrane 100 that faces chamber 68, support 110 may alternatively be on the side of membrane 100 that faces chamber 66.

For some applications, membrane 100 may comprise a 2D material, such as graphene (i.e., a graphene-based membrane) or boron nitride. For some applications, membrane 100 may comprise carbon nanotubes, titanium dioxide, hafnium dioxide, aluminum oxide, polycarbonate, polymethylmethacrylate (PMMA), polydimethylsiloxane (PDMS), or any suitable substance. For some applications, membrane 100 may be metallic (e.g., comprising gold). For any such application, a support similar to support 110 (mutatis mutandis) may or may not be used.

As described hereinabove, for applications in which cartridge 60 is provided with membrane 100 intact, formation of a nanopore 104 in membrane 100 is achieved by application of a voltage between electrodes 76 and 78. This process is known as dielectric breakdown (DB). For nanopore-based assays, it is important to know and/or control the size, shape, and/or location of the nanopore being used. Using existing DB techniques, the size, shape, and location of DB-created nanopores are typically inconsistent and/or unknown.

For some applications, a protective (e.g., electrically-insulating) film 120 covers at least one side (e.g., at least one surface) of membrane 100, except for an aperture 122 in the film, through which the surface of the membrane is exposed. Typically, film 120 defines exactly one aperture 122. Film 120 protects (e.g., electrically insulates) the majority of the surface area of membrane 100, while leaving a small target region 103 of the membrane exposed at aperture 122, DB occurring only within the target region. Film 120 therefore serves as a resist for DB. It is hypothesized by the inventors that film 120 increases control and/or consistency of the size, shape, and/or location of nanopores formed by DB, e.g., as described hereinbelow.

As shown, for some applications in which both support 110 and film 120 are used, support 110 is disposed on one side of membrane 100, film 120 is disposed on the opposite side of the membrane, and aperture 122 is aligned with window 112 (i.e., opposite the window). Typically, a width (e.g., a diameter) d3 of aperture 122 is smaller than width d5 of window 112 (e.g., d3 may be less than 50% of d5, e.g., less than 20 percent of d5, e.g., less than 10 percent of d5, e.g., less than 5 percent of d5, e.g., less than 1 percent of d5, e.g., less than 0.1 percent of d5, e.g., as less than 0.01 percent of d5, such as less than 0.001 percent of d5). Therefore aperture 122 in film 120 provides greater control over the size, shape, and/or location of the nanopore than does window 112 alone.

For some applications in which both support 110 and film 120 are used, support 110 and film 120 are both disposed on the same side of membrane 100, e.g., with aperture 122 disposed within window 112. For some such applications, film 120 is disposed on membrane 100 only within zone 102.

Irrespective of whether support 110 is used, for some applications in which film 120 is disposed on only one side of membrane 100, the film is disposed on the side of the membrane that faces sample chamber 66 (i.e., the sample-side of the membrane), and for other applications the film is disposed on the side of the membrane that faces second chamber 68.

Alternatively, film 120 is disposed on both sides of membrane 100, e.g., with two apertures aligned opposite each other.

Film 120 has a thickness d4 that is typically greater than 1 nm and/or less than 10 microns (e.g., 1-10,000 nm, such as 10-10,0000 nm, e.g., 0.1-10 microns).

For some applications, film 120 is an electron-sensitive film, and aperture 122 is formed by electron-beam lithography (e-beam lithography). Because e-beam lithography can provide sub-10 nm resolution, it can be used to form a small aperture having a known shape (e.g., circular). Alternatively or additionally aperture 122 may be formed by Focused Ion Beam (FIB) lithography or milling. Alternatively or additionally aperture 122 may be formed by etching.

Materials from which film 120 may be formed include those used in the art of chip fabrication.

An example of unknown and/or inconsistent nanopore characteristics is that, although conductivity across the membrane being nanoporated may provide an indication of the cross-sectional area of the created nanopore, it does not necessarily provide an indication of its shape. For instance, a circular nanopore may provide similar conductivity to an elongate nanopore, e.g., that has a similar cross-sectional area.

Reference is further made to FIGS. 8A-B, and 9A-B. For some applications, aperture 122 has a width d3, shape, and/or position similar to that which is desired for the nanopore that will be formed in membrane 100, such that aperture 122 serves as a stencil for the nanopore. For example, width d3 may be no more than 100 percent (e.g., no more than 50 percent, e.g., no more than 30 percent, e.g., no more than 10 percent, such as no more than 5 percent) greater or smaller than the width that is desired for the nanopore that will be formed. For such applications, width d3 is typically greater than 0.1 nm and/or smaller than 1 micron (e.g., 0.001-1 micron, e.g., 1-500 nm, such as 2-100 nm). FIGS. 8A-B are schematic illustrations that show the site of nanoporation before (FIG. 8A) and after (FIG. 8B) formation of a nanopore 104, in accordance with some such applications of the invention. In FIGS. 8A-B, width d3 of aperture 122 is slightly greater than a width d6 of nanopore 104.

For some applications, rather than serving as a stencil, aperture 122 merely delineates a target region of membrane 100 in which a nanopore may be formed. For such applications, width d3 may be more than 10 times greater (e.g., more than 100 times greater, such as more than 1000 times greater) than that which is desired for the nanopore that will be formed in membrane 100. Nonetheless, width d3 is still typically smaller than that of window 112. For some such applications, width d3 is greater than 100 nm and/or less than 10 microns (0.1-10 microns, e.g., 0.3-10 microns, e.g., 0.3-1 micron). FIGS. 9A-B are schematic illustrations that show the site of nanoporation before (FIG. 9A) and after (FIG. 9B) formation of a nanopore 104, in accordance with some such applications of the invention. In FIGS. 9A-B, width d3 of aperture 122 is significantly greater than a width d6 of nanopore 104.

Figure 3:
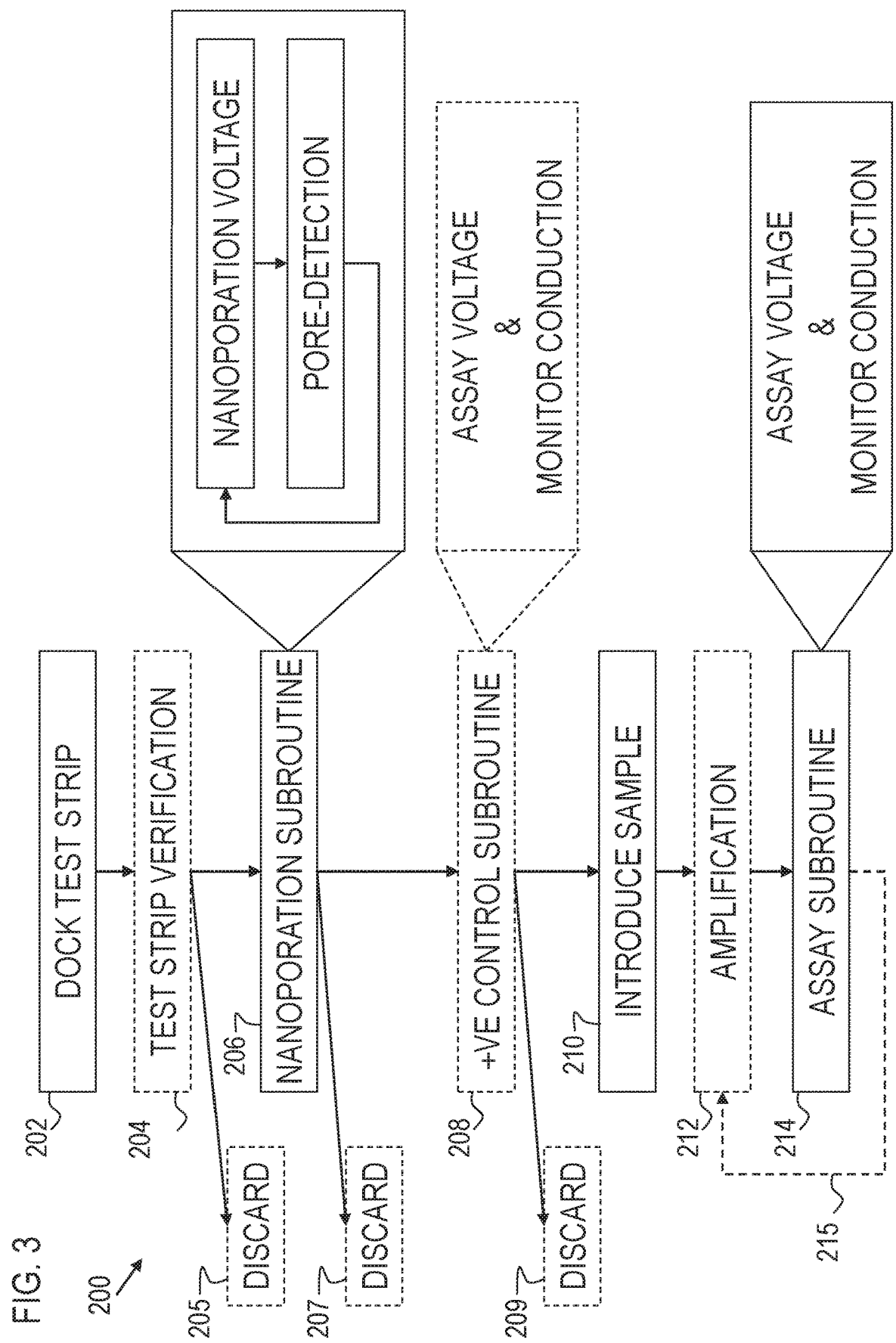
FIG. 3 is a flowchart showing at least some steps in a technique for nanopore-based assaying, in accordance with some applications of the invention.

Reference is now made to FIG. 3, which is a flowchart showing at least some steps in a technique 200 for nanopore-based assaying, in accordance with some applications of the invention. Technique 200 is typically used with system 20, but for some applications the technique, or steps thereof, may be used with other apparatus. The use of broken lines in FIG. 3 is intended to indicate steps that are optional.

Test cartridge 60 is docked with dock 40 of device 30, thereby placing terminals 86 and 88 of the cartridge into electrical contact with terminals 46 and 48 of the dock (step 202).

For some applications, device 30 (e.g., circuitry 34 thereof) verifies cartridge 60—e.g., verifies an attribute of the cartridge, such as the identity and/or state of the cartridge (step 204). For example, device 30 may verify (i) that cartridge 60 has been correctly docked (e.g., by testing contact between the dock-terminals and the cartridge-terminals), (ii) that membrane 100 is intact and/or contains no nanopores (e.g., by testing conductivity between electrodes 76 and 78), (iii) that cartridge 60 is of the correct brand, and/or (iv) that the cartridge (e.g., the membrane thereof) is of the correct type for the test being performed. For some applications, verification step 204 includes measuring capacitive current induced across membrane 100 by a voltage applied between electrodes 76 and 78.

Figure 4:
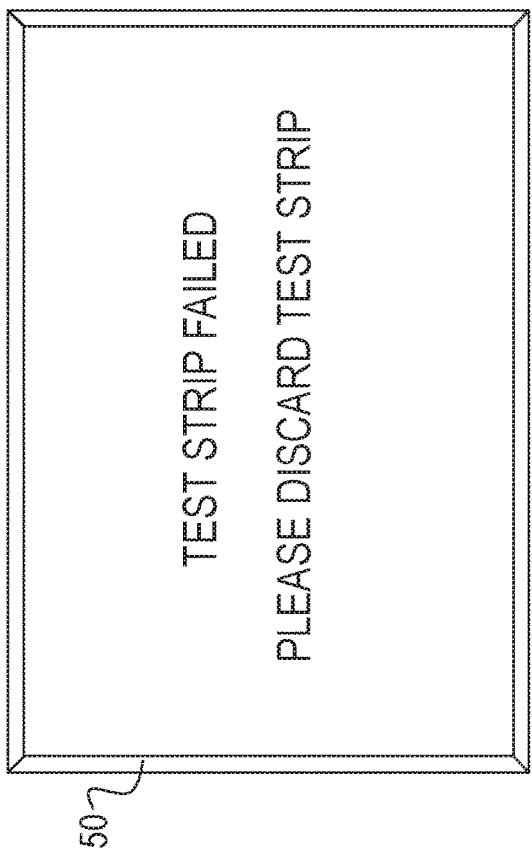
FIGS. 4-7 are schematic illustrations of a user interface, in accordance with some applications of the invention.
Figure 5:

FIG. 4 is a schematic illustration of UI 50, in accordance with some applications of the invention, displaying the results of a successful verification step 204, and prompting the user to proceed. Typically, if cartridge 60 does not pass verification (e.g., because membrane 100 is not intact and/or already contains a nanopore), the device does not proceed (or does not allow the user to proceed) to subsequent steps, and/or prompts the user to remove and discard test cartridge 60. FIG. 5 is a schematic illustration of UI 50 displaying such a prompt, in accordance with some applications of the invention. This discard function is represented by step 205.

Subsequently, device 30 (e.g., circuitry 34 thereof) performs a nanoporation subroutine (step 206). For some applications, device 30 performs the nanoporation subroutine automatically in response to cartridge 60 being docked with dock 40. For some applications, device 30 performs the nanoporation routine only upon input from the user (e.g., pressing of the button shown in FIG. 4). The nanoporation subroutine comprises: (i) applying a nanoporation voltage between dock-terminals 46 and 48 (the voltage thereby also being applied between electrodes 76 and 78), and (ii) detecting conduction of a pore-detection current between the dock-terminals (the current thereby also being conducted between electrodes 76 and 78). The pore-detection current is the result of device 30 applying a pore-detection voltage between the dock-terminals (the pore-detection voltage thereby also being applied between electrodes 76 and 78). The nanoporation voltage is configured to create a nanopore in membrane 100 via dielectric breakdown (DB), e.g., as described hereinabove. Successful formation of a nanopore enables conduction of the pore-detection current (e.g., above a threshold amplitude), and therefore detection of this conduction indicates successful formation of a nanopore. By detecting (and typically analyzing) the pore-detection current, device 30 identifies whether nanoporation has been successful (e.g., whether a nanopore has been created, and optionally whether the nanopore is of the correct size). Typically, parts i and ii of the nanoporation subroutine are alternated, e.g., with pore-detection occurring during interruptions in the nanoporation voltage. For some applications, application of the pore-detection voltage alternates with application of the nanoporation voltage. Alternatively, the pore-detection voltage may be applied continuously, even though detection of pore-detection current is only performed during interruptions in the nanoporation voltage. Typically, parts i and ii of the nanoporation subroutine are repeated iteratively until device 30 verifies that nanoporation has been successful.

For some applications, the nanoporation voltage is greater than 0.01 V DC (e.g., greater than 0.1 V DC, e.g., greater than 1 V DC, e.g., greater than 5 V DC, such as greater than 10 V DC) and/or less than 100 V DC (e.g., less than 50 V DC, such as less than 30 V DC). For example, the nanoporation voltage may be 0.01-100 V DC (e.g., 1-50 V DC, e.g., 5-30 V DC, e.g., 6-18 V DC, such as 10-15 V DC).

For some applications, the pore-detection voltage is greater than 10 mV DC (e.g., greater than 30 mV DC, e.g., greater than 50 mV DC, e.g., greater than 80 mV DC, such as greater than 100 mV DC) and/or less than 1 V DC (e.g., less than 700 mV DC, e.g., less than 500 my DC, e.g., less than 300 mV DC, such as less than 200 mV DC). For example, the pore-detection voltage may be 0.01-1 V DC (e.g., 10-900 mV DC, e.g., 10-500 mV DC, e.g., 50-300 mV DC, e.g., 100-200 mV DC).

For some applications, the nanoporation voltage and the pore-detection voltage are the same, and device 30 identifies successful nanopore creation by detection of current induced by this voltage. That is, for some applications, for nanoporation subroutine 206, the pore-detection current is the current induced by the nanoporation voltage once a nanopore has been formed. For some such applications, device 30 monitors for the pore-detection current continuously while the nanoporation voltage is applied.

For some applications, the amplitude of the pore-detection current that is indicative of successful nanoporation is above 10 picoamps (pA) and/or below 1 milliamp. For some applications, the polarity of the pore-detection voltage is the same as the polarity of the nanoporation voltage. For some applications, the polarity of the pore-detection voltage is the opposite of the polarity of the nanoporation voltage. Nanoporation subroutine 206, according to some applications of the invention, is described in more detail hereinbelow.

For some applications, device 30 (e.g., circuitry 34 thereof) has a discard function 207, whereby if the device detects that membrane 100 has been damaged or overporated (e.g., because conduction of the pore-detection current is above an upper threshold), the device does not proceed (or does not allow proceeding) to subsequent steps, and/or prompts the user to remove and discard test cartridge 60 (e.g., as shown in FIG. 5). For some applications, discard function 207 is similar to discard function 205, mutatis mutandis. For example, both may utilize detection of the pore-detection current to verify the condition of membrane 100. However, function 207 may use a conduction threshold (above which function 207 is triggered) that is higher than a conduction threshold of function 205. For example, whereas function 205 typically rejects a cartridge 60 whose membrane 100 contains any nanoporation, function 207 typically only rejects a cartridge whose membrane has excessive nanoporation.

For some applications, a positive-control subroutine 208 is performed. As described hereinabove, for some applications, conduction-based testing of a nanopore may not reveal all of the relevant characteristics of the nanopore, such as the shape of the nanopore, or its suitability for detection of a specific analyte. It is hypothesized by the inventors that it is particularly important to characterize the nanopore when performing quantitative analyses. For example, it is hypothesized by the inventors that by using a positive-control moiety that is chemically, electrochemically, and/or sterically similar to the analyte, it is possible to improve the accuracy of the quantitative analysis. In step 208, application of an assay voltage and detection of conduction between electrodes 76 and 78 are typically performed in the same way as in assay subroutine 214 that will subsequently be used to test the actual sample, mutatis mutandis. However, in step 208, the positive-control moiety, but not the sample, is available for translocation across membrane 100. This is typically achieved by the positive-control moiety, but not the sample, being disposed within internal space 64.

For applications in which a positive-control moiety is used, cartridge 60 is typically provided with the positive-control moiety present in internal space 64 at a known concentration. Alternatively, the positive-control moiety may be provided separately, and is introduced into internal space 64 by the user or by device 30.

Typically, the positive-control moiety is disposed within (or is introduced into) sample chamber 66, and system 20 is configured to cause the positive-control moiety to translocate across membrane 100 toward chamber 68—i.e., in the same direction as the analyte will subsequently translocate. This patent application generally relates to this arrangement for the positive-control moiety. For applications in which a positive-control moiety is used in this arrangement, cartridge 60 is typically provided with the positive-control moiety present in chamber 66 at a known concentration. Alternatively, the positive-control moiety may be provided separately, and is introduced into chamber 66 by the user (e.g., via port 70) or by device 30.

For some applications, the positive-control moiety is disposed within (or is introduced into) sample chamber 68, and system 20 is configured to cause the positive-control moiety to translocate across membrane 100 toward chamber 66—i.e., in the opposite direction to the analyte. For applications in which a positive-control moiety is used in this arrangement, cartridge 60 is typically provided with the positive-control moiety present in chamber 68 at a known concentration. Alternatively, the positive-control moiety may be provided separately, and is introduced into chamber 68 by the user or by device 30 (e.g., via a dedicated port). For some applications in which a positive-control moiety is used in this arrangement (e.g., for applications in which the positive-control moiety has the same charge polarity as the analyte), the assay voltage used for positive-control subroutine 208 has the opposite polarity to that of the assay voltage used for assay subroutine 214.

For applications in which step 208 is performed, device 30 is typically configured to automatically self-calibrate and/or adjust (e.g., standardize) the raw data that will be obtained during assay subroutine 214, based on the results of step 208. Alternatively or additionally, device 30 may be configured to reject cartridge 60 if the results of step 208 are not satisfactory. This discard function is represented by step 209.

Although FIG. 3 shows the optional use of a positive control being a distinct step 208 that is performed before the assay subroutine 214 (and even before the sample is introduced to cartridge 60), it is to be noted that, for sonic applications, the scope of the invention includes using a positive control simultaneously with testing the sample, e.g., by multiplexing. For example, the analyte may be tagged with a first tag, and the positive-control moiety may be tagged with a second, different tag, with device 30 being able to distinguish between the passage of the first-tag-tagged-control through the nanopore, and the passage of the second-tag-tagged analyte through the nanopore.

Figure 6:
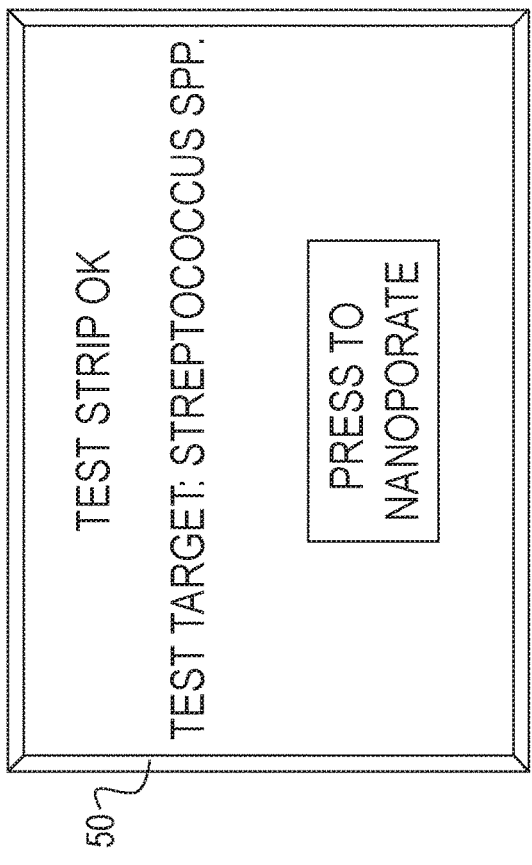

The sample to be assayed is introduced via port 70 into chamber 66 of cartridge 60 (step 210). FIG. 6 is a schematic illustration of UI 50 displaying a prompt for the user to introduce the sample and to press "proceed," in accordance with some applications of the invention. For applications that include step 208, this prompt is typically displayed after step 208 is complete. For applications that do not include step 208, this prompt is typically displayed after step 206 is complete, in response to verification of successful nanoporation.

For applications in which the analyte is or includes a nucleic acid, nucleic acid extraction and/or purification are typically performed prior to introduction of the sample.

For some applications in which the analyte is or includes a nucleic acid, amplification of the analyte sequence is typically performed prior to testing, in order to achieve a sufficient frequency of translocation events. For some such applications, this amplification is performed prior to introduction of the sample. For some such applications, a kit is provided that includes at least one appropriate nucleic acid primer and a polymerase, e.g., in addition to test cartridge 60.

For applications in which the nucleic acid is or includes RNA, reverse transcription is typically performed to facilitate amplification.

For some applications in which the analyte is or includes a nucleic acid, and as shown, amplification of the analyte sequence is performed after step 210, once the sample is already within cartridge 60 (step 212). For some such applications, cartridge 60 is provided with a polymerase and/or at least one nucleic acid primer already present in internal space 64 (e.g., chamber 66). Alternatively, the polymerase and/or at least one nucleic acid primer may be introduced by the user via port 70, or by device 30. For some applications in which amplification of the analyte sequence is performed after step 210, device 30 comprises a heater 42 within or adjacent to dock 40, configured to heat cartridge 60 (e.g., internal space 64 thereof, such as chamber 66) in order to facilitate the nucleic acid amplification. Device 30 may also comprise a cooler to cool cartridge 60. For some applications (e.g., for PCR-based amplification) device 30 performs repeated heat-cool thermal cycles. For some applications (e.g., for isothermal nucleic acid amplification, such as LAMP, NEAR, and RPA), repeated cycling is not necessary.

For applications in which the analyte is or includes a nucleic acid, and in which amplification of the analyte sequence is performed once the sample is already within cartridge 60, device 30 typically performs the assay subroutine (step 214) automatically after amplification step 212 is complete. Alternatively, device 30 may provide another prompt on UI 50, prompting the user to proceed to step 214.

For some applications in which the analyte is or includes a nucleic acid, and in which amplification of the analyte sequence is performed once the sample is already within cartridge 60, assay subroutine 214 is performed multiple times, after increasing amounts of amplification have been achieved. This is represented in FIG. 3 by arrow 215, which implies iterations of discrete steps 212 and 214. However, the scope of the invention includes performing assay subroutine 214 multiple times without interrupting the amplification process. It is hypothesized by the inventors that, for some applications, performing multiple assays after different amounts of amplification may increase the accuracy and/or quantitativeness of technique 200.

During assay subroutine 214, device 30 (e.g., circuitry 34 thereof), via contact between the dock-terminals and the cartridge-terminals, (i) applies an assay voltage between electrodes 76 and 78, and (ii) simultaneously detects conduction of a current between the electrodes—e.g., a current resulting from the application of the assay voltage. Translocation of a molecule into (e.g., through) the nanopore is known as a translocation event, and as each molecule of the analyte translocates, the molecule at least partly obstructs the path of conduction through the nanopore, and conduction through the nanopore therefore drops (e.g., transiently). Each drop is registered as a translocation event signal.

Characteristics of each translocation event signal, such as its magnitude, frequency, duration, charge (the integral of the signal), and/or power, are indicative of the molecule that translocated. Analysis of the translocation event signals received over a period of time (e.g., several nanoseconds, several microseconds, several milliseconds, several seconds, several minutes, or several hours) provides an indication of a concentration of the analyte in the sample (e.g., whether the analyte is present in a concentration that is greater than a predetermined threshold concentration). It is to be noted that in this context (including the specification and the claims), determining and/or indicating a concentration of the analyte includes determining and/or indicating a presence or absence of the analyte.

For some applications, the translocation of molecules of the sample (including molecules of the analyte) through the nanopore is induced by application of a voltage between electrodes 76 and 78. For such applications, the analyte is typically a charged molecule. For some such applications, the voltage that induces the translocation is the assay voltage itself, and the assay voltage may therefore be considered to be a translocation voltage. For some such applications, for detecting translocation events, device 30 detects conduction of a signal modulated onto the translocation voltage.

Alternatively, a separate translocation current may be used. For some such applications separate translocation current is driven between and detected via one or more additional electrodes within the chambers, e.g., between a first additional electrode within chamber 66, and a second additional electrode within chamber 68 (not shown). For applications in which additional electrodes are used, cartridge 60 and dock 40 typically have corresponding additional terminals.

For some applications, the assay voltage is 0.01-5 V DC (e.g., 0.01-1 V DC, e.g., 10-500 mV DC, e.g., 50-300 mV DC, e.g., 100-200 mV DC). For some applications, the polarity of the assay voltage is the same as the polarity of the nanoporation voltage. For some applications, the polarity of the assay voltage is the opposite of the polarity of the nanoporation voltage.

For some applications, translocation of the analyte through the nanopore may occur independently of an applied voltage (e.g., without application of a translocation voltage). For example, the analyte may move along a concentration, pressure, salt, and/or heat gradient.

Although the above description describes both the nanoporation voltage and the assay voltage being applied between the same pair of electrodes (electrodes 76 and 78), for some applications the nanoporation voltage and the assay voltage are applied between different respective pairs of electrodes. For such applications, cartridge 60 and dock 40 typically have corresponding additional terminals.

Figure 7:
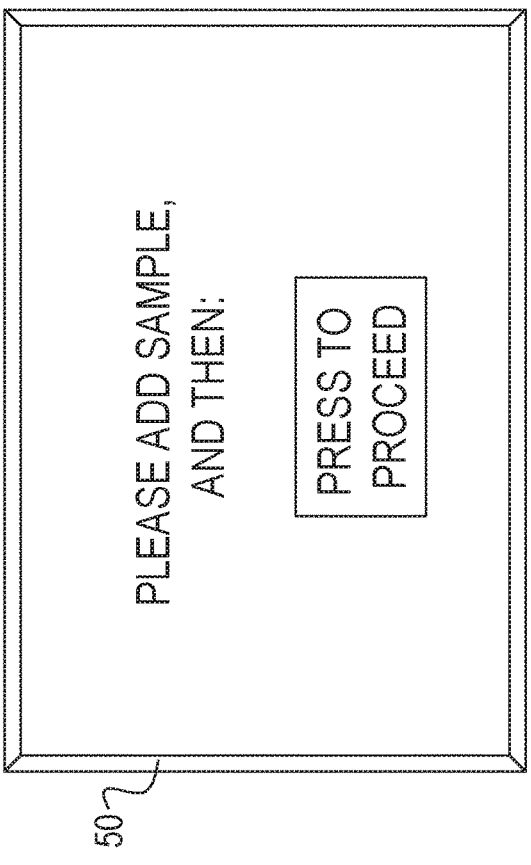

Once assay subroutine 214 is complete, device 30 displays the result on UI 50. FIG. 7 is a schematic illustration of UI 50 displaying an example of such a result, in accordance with some applications of the invention. As shown, the result may indicate an identified target (e.g., a pathogen), and may indicate a confidence level. The result may additionally or alternatively provide details regarding the detected analyte, such as the concentration of the analyte in the sample.

Typically, for applications in which positive-control subroutine 208 is performed using a positive-control moiety within chamber 66, both the sample and the positive-control moiety are present within the chamber during assay subroutine 214. For some such applications, the concentration of the positive-control moiety is negligible compared to the expected concentration of the analyte, and the positive-control moiety can therefore be ignored. For sonic applications, device 30 (e.g., circuitry 34 thereof) is configured to record translocation event data obtained during positive-control subroutine 208, and to use this recorded positive-control data to increase the accuracy of assay data obtained during subroutine 214. For example, device 30 may deduct a value of the recorded positive-control data (e.g., the frequency of translocation events) from a corresponding value of the assay data, in order to obtain a net value that is attributable to true translocations of the analyte. For some applications, multiplexing may be used to distinguish translocation events of the positive-control moiety from translocation events of the analyte, e.g., by using different tags.

It is to be noted that the positive-control moiety and subroutine may be used with other nanopore-based test cartridges (e.g., those provided with an existing nanopore), devices, and techniques. There is therefore provided, in accordance with some applications of the invention, apparatus for facilitating nanopore-based detection of an analyte in a sample, the apparatus comprising:

a casing that defines an internal space;

a membrane having a thickness of 0.1 nm-1 micron, the membrane disposed inside the casing, and separating the internal space into a sample chamber and a second chamber, and the casing shaped to define a port via which the sample is introducible into the sample chamber, a first electrode, disposed within the sample chamber;

a first cartridge-terminal, electrically connected to the first electrode, and accessible from outside of the cartridge;

a second electrode, disposed within the second chamber;

a second cartridge-terminal, electrically connected to the second electrode, and accessible from outside of the cartridge; and a positive-control moiety having a known concentration, disposed in the internal space, the positive-control moiety being a positive control for the analyte.

It is to be noted that although FIG. 3 shows sample-introduction step 210 being subsequent to nanoporation subroutine 206, for some applications, the sample is added before subroutine 206. For some such applications, the sample is added before test cartridge 60 is docked with dock 40.

Returning now to nanoporation subroutine 206. As described hereinabove, the nanoporation voltage is typically applied iteratively, e.g., until device 30 verifies that nanoporation has been successful. For some applications of the invention, the nanoporation voltage (e.g., its magnitude and/or duration) is different during different iterations, e.g., in response to device 30 determining that previous iterations had not successfully created a nanopore. For example, the nanoporation voltage may initially be applied at a first magnitude for a first duration, and may subsequently be applied at a different magnitude and/or for a different duration. One particular example configuration is one or more iterations at a first magnitude of 4-8 V (e.g., 5-7 V, such as about 6 V); followed, if successful nanoporation has still not been verified, by one or more iterations at a second magnitude of 10-14 V (e.g., 11-13 V, such as about 12 V); followed, if successful nanoporation has still not been verified, by one or more iterations at a third magnitude of 16-20 V (e.g., 17-19 V, such as about 18 V).

Returning now to verification step 204. As described hereinabove, for applications in which cartridge 60 is provided with membrane 100 intact, device 30 (e.g., circuitry 34 thereof) is typically configured to perform a nanoporation subroutine (e.g., nanoporation subroutine 206) and a nanopore-based assaying subroutine (e.g., assay subroutine 214) while dock-terminals 46 and 48 remain in electrical contact with cartridge-terminals 86 and 88 (i.e., without contact being broken). For some such applications, device 30 is configured in this manner at least in part by verification step 204. For example, if, after nanoporation subroutine 206 but before assay subroutine 214, cartridge 60 were to be undocked and redocked (thereby breaking and remaking contact between the dock-terminals and the cartridge-terminals), the verification step would determine that a nanopore already exists in membrane 100, and the cartridge would be rejected. Similarly, the requirement that, for a newly-docked (or newly-redocked) cartridge 60, device 30 begins technique 200 at least as early as nanoporation subroutine 206, means that device 30 is configured specifically to perform both nanoporation and nanopore-based assaying. Such a configuration thereby renders device 30 incapable of performing a nanopore-based assay using a given test cartridge without first performing nanoporation on that test cartridge.

Returning now to discard functions 205, 207, and 209. The sensing of continued electrical contact between the dock-terminals and the cartridge-terminals may also facilitate these discard functions. For example, for some applications, device 30 may be configured to retain the discard prompt, and/or to prevent proceeding to subsequent steps, until the test cartridge has been removed—which is detected as a break in electrical contact between the dock-terminals and the cartridge-terminals.

For some applications, device 30 uses a method other than sensing continued electrical contact between the dock-terminals and the cartridge-terminals for detecting the continued presence of cartridge 60 (ire., whether cartridge 60 has been removed). For example, dock 40 may include a sensor (e.g., a switch) that is maintained in a particular state by the continued presence of cartridge 60 at (e.g., in) dock 40.

Reference is now made to FIGS. 10A-B, which are schematic illustrations showing surface modification of membrane 100, in accordance with some applications of the invention. For some applications, a surface modification 106 of membrane 100 is made in order to influence the translocation of the analyte through nanopore 104. Typically, membrane 100 (e.g., cartridge 60) is provided with modification 106 already made (FIG. 10A), and nanopore 104 is formed subsequently (FIG. 10B).

For some applications, such modifications are configured to affect the rate at which the analyte translocates through the nanopore. For example, an increased affinity for the analyte may increase the duration that each translocating analyte molecule obstructs electrical conduction through the nanopore (e.g., the duration that the molecule is disposed within the nanopore), thereby increasing the duration of the translocation event signal. Alternatively or additionally, such modifications are configured to affect (e.g., increase) the degree to which the translocating molecule obstructs current conduction as the molecule translocates, thereby increasing the amplitude of the translocation event signal. It is hypothesized by the inventors that increasing the duration and/or amplitude of translocation event signals improves detection of the signals generally, and that doing this specifically for translocations of the analyte improves specificity (e.g., distinguishing true translocations of the analyte from background noise). For some applications, the modifications introduce new blockage levels within each translocation event signal. For example, reversible annealing between an analyte DNA strand and a membrane-modifying DNA strand may affect current conduction amplitude to different degrees during different portions of an individual translocation event, thereby giving the translocation event signal a distinct "signature."

It is hypothesized by the inventors that some surface modifications (e.g., prior art surface modifications) that bind the analyte may disadvantageously "mop up" the analyte, reducing the availability of the analyte within sample chamber 66, and thereby adversely affecting detection. For some applications of the invention, and as shown, surface modification 106 is only present and/or exposed at target region 103, which, compared to the overall surface area of membrane 100, has a much smaller surface area exposed to sample chamber 66, thereby advantageously diminishing this potential problem. This is typically achieved by making modification 106 after film 120 is in place and aperture 122 is formed, thereby only modifying membrane 100 at target region 103. Alternatively, modification 106 may be made over a larger area of membrane 100 (e.g., all of the membrane), and be subsequently covered by film 120 except for at target region 103.

Typically, modification 106 is made by binding a chemical moiety to the surface of the membrane.

There is therefore provided, in accordance with some applications of the invention, apparatus comprising (i) a membrane having a thickness of 0.1 nm-1 micron; and (ii) an electrically-insulating film having a thickness of 1 nm-10 microns, coating a surface of the membrane, and shaped to define an aperture through the film, such that a target region of the surface is exposed through the aperture, wherein chemistry of the surface at the target region is modified by a chemical moiety that is bound to the surface only at the target region.

For applications in which surface modification 106 is only present and/or available at target region 103, surface modification 106 is therefore made on the side(s) of membrane 100 on which film 120 is disposed.

Examples of chemical moieties that may be used for modification 106 include: silane, thiols, amino acids, carboxylic acids, azides, amides, sugars (e.g., polysaccharides and/or a specific sugar), immunoglobulins antibodies), nucleic acids (e.g., oligonucleotides, such as aptamers), and peptide nucleic acids.

For sonic applications, the modification increases an affinity of the surface of membrane 100 for immunoglobulins, nucleic acids (e.g., having a particular sequence), polypeptides, sugars (e.g., polysaccharides), aldehydes, ketones, alkynes, azides, esters, carboxyls, boric acid, methoxyethene, and/or epoxies. For some applications, the modification changes (e.g., increases or decreases) hydrophilicity of the surface of membrane 100.

Reference is now made to FIGS. 11A-B, which are schematic illustrations showing surface modification 106 of membrane 100, in accordance with some applications of the invention. FIG. 11A shows before nanoporation, and FIG. 11B shows after nanoporation. For some applications, film 120 is disposed only on the side of membrane 100 that faces chamber 66, and surface modification 106 is made on the opposite side of the membrane, typically over a larger area of the membrane (e.g., all of the membrane). It is hypothesized by the inventors that making modification 106 only outside of sample chamber 66 is an alternative solution to the potential problem described hereinabove, in which an analyte-binding modification within the sample chamber may otherwise disadvantageously "mop up" analyte within the sample chamber.

For some applications, a surface modification is made both (i) within target region 103 (e.g., as shown in FIGS.

10A-B), and (ii) on the other side of membrane 100 (e.g., as shown in FIGS. 11A-B), mutatis mutandis. For some such applications, the same modification is made in both of these places. Alternatively, a different modification is made in each of these places.

Reference is now made to FIGS. 12A-C, which are schematic illustrations showing surface modification 106 of membrane 100, in accordance with some applications of the invention. For some applications, surface modification 106 is made subsequently to formation of nanopore 104 (e.g., subsequently to nanoporation subroutine 206). For example, the chemical moiety or moieties that will modify the surface of membrane 100 (optionally with one or more accessory substances that facilitate the modifying of the surface) may be introduced into internal space 64 by the user (e.g., via port 70) or by device 30. For some such applications, a kit is provided that includes cartridge 60 and, separately, the chemical moiety or moieties (optionally with the one or more accessory substances).

FIG. 12A shows before nanoporation, FIG. 12B shows after nanoporation but before surface modification, and FIG. 12C shows after surface modification. It is hypothesized by the inventors that, for some applications, performing surface modification after nanoporation facilitates surface modification within aperture 104 (i.e., within the lumen of the aperture), e.g., in addition to the surface on the side of membrane 100. FIG. 12C shows modification 106 (i) on the sample-side of membrane 100, and (ii) within the lumen of aperture 104.

Figure 13:
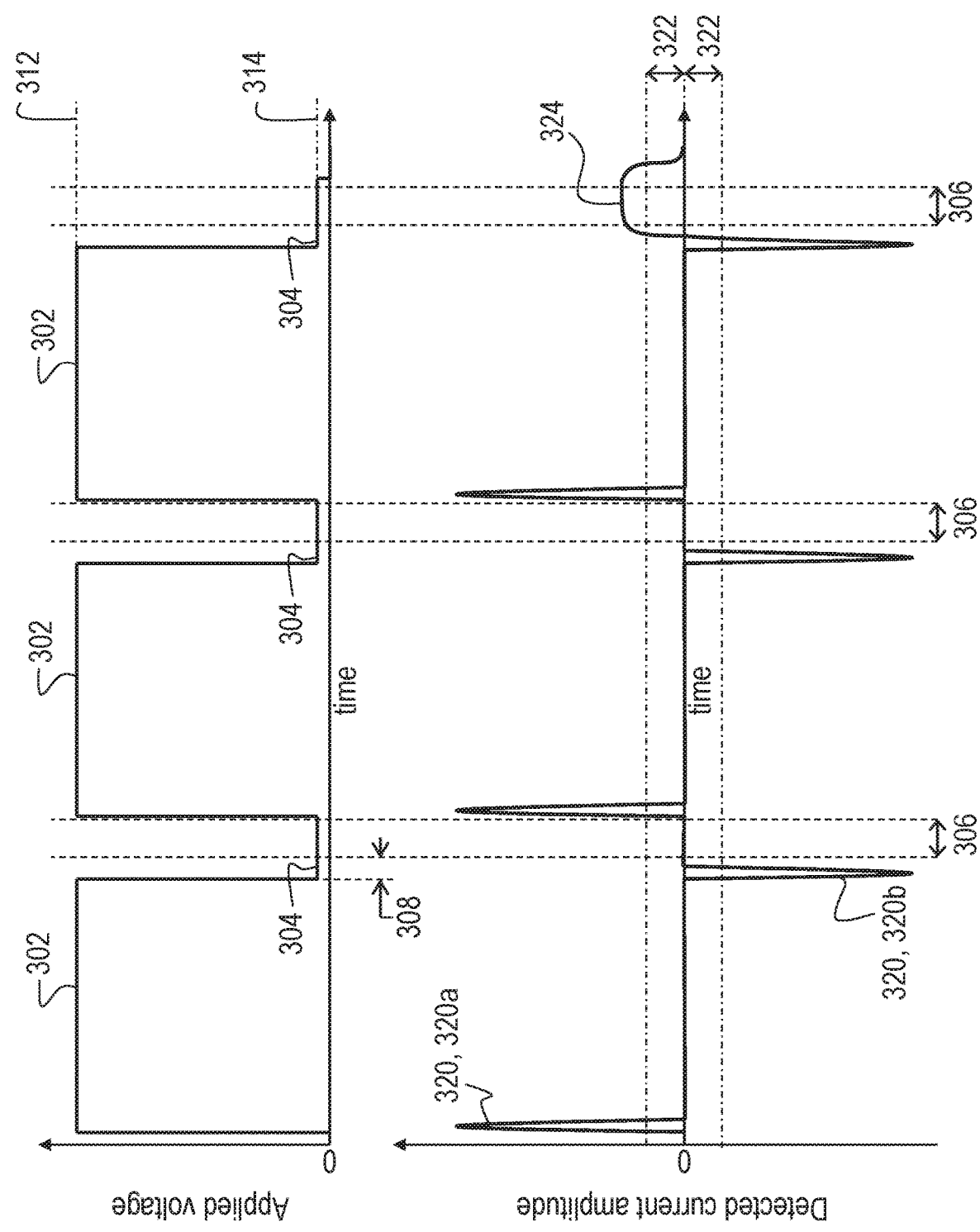
FIG. 13 is a schematic illustration showing applied voltage and detected current during a nanoporation subroutine, in accordance with some applications of the invention.
Figure 14:
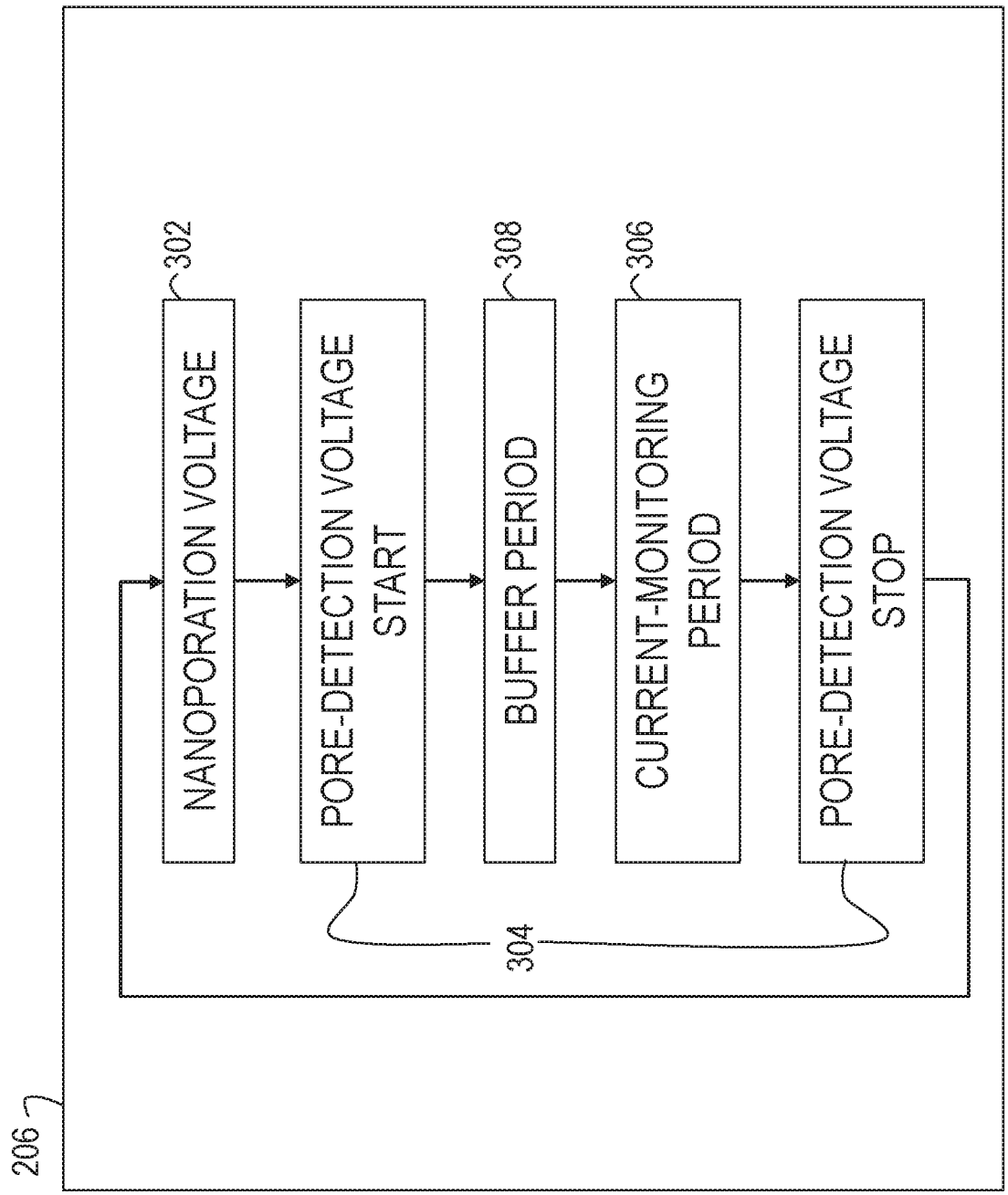
FIG. 14 is a flow chart showing at least some steps within the nanoporation subroutine, in accordance with some applications of the invention.

Reference is now made to FIGS. 13 and 14. FIG. 13 is a schematic illustration showing applied voltage and detected current during nanoporation subroutine 206, in accordance with some applications of the invention. FIG. 14 is a flow chart showing at least some steps within nanoporation subroutine 206, in accordance with some applications of the invention. As described hereinabove, during nanoporation subroutine 206 (i) application of the nanoporation voltage, and (ii) detection of conduction of the pore-detection current are performed iteratively until the detected pore-detection current indicates that a nanopore has been created. The periods during which detection of conduction of the pore-detection current is performed, are referred to herein as current-detection periods 306.

Purely for illustrative purposes, FIG. 13 shows a nanoporation subroutine that includes three iterations.

The upper part of FIG. 13 schematically illustrates alternating application of a nanoporation voltage 302 having a nanoporation magnitude (i.e., voltage) 312, and application of a pore-detecting voltage 304 having a smaller pore-detection magnitude 314.

The lower part of FIG. 13 schematically illustrates the amplitude of the current that is detected during the same period. It has been observed by the inventors that a change in the magnitude of a voltage applied across membrane 100 typically induces a transient capacitive current 320 across the membrane, which is detectable via electrodes 76 & 78. This is illustrated in FIG. 13 by (i) a positive-polarity current spike 320a occurring upon each increase of the applied voltage to nanoporation magnitude 312, and (ii) a negative-polarity current spike 320b occurring upon each decrease of the applied voltage to pore-detection magnitude 314.

Typically, device 30 (e.g., circuitry 34 thereof) is configured with a threshold amplitude 322 of the detected current, the threshold amplitude being indicative of successful nanoporation, such that when the detected current exceeds the threshold amplitude the device ends nanoporation subroutine 206. Threshold amplitude 322 is typically indifferent to polarity. It has been observed by the inventors that capacitive current spikes may exceed threshold amplitude 322, and may therefore be misinterpreted as being a nanopore-detection current of greater-than-threshold amplitude, indicative of successful nanoporation. That is, capacitive current spikes may, in principle, trigger false positives of nanopore formation.

For some applications, device 30 (e.g., circuitry 34 thereof) is configured to provide a buffer period 308 between changes in the applied voltage, and current-detection periods 306, in order that the capacitive current spikes are not read. That is, during buffer period 308, the amplitude of the current is ignored. In particular, because nanopore detection is based on detection of current induced by pre-detecting voltage 304, for some applications device 30 is configured to provide buffer period 308 between (i) the start of the application of pore-detection voltage 304, and (ii) the start of current-monitoring period 306. Similarly, current-monitoring period typically ends prior to the start of the application of nanoporation voltage 302.

Buffer period 308 is typically greater than 0.01 s (e.g., greater than 0.1 s, such as greater than 1 s) and/or shorter than 300 s (e.g., shorter than 30 s, e.g., shorter than 20 s, e.g., shorter than 10 s, such as shorter than 5 s), such as 0.1-5 s.

In the example shown in FIG. 13, successful nanoporation is achieved after three applications of nanoporation voltage 302, and therefore in response to the third application of pore-detection voltage 304, the amplitude of the (pore-detection) current exceeds threshold 322. Because this amplitude is that of the (ionic) pore-detection current through the newly-formed nanopore, it is maintained for as long as the pore-detection voltage is maintained, and is therefore detected during the subsequent current-detection period 306. Reference numeral 324 indicates where this occurs. As described hereinabove, upon detecting the greater-than-threshold pore-detection current, device 30 (e.g., circuitry 34 thereof) terminates nanoporation subroutine 206.

It is to be noted that, although FIG. 13 shows seamless transitions between nanoporation voltage 302 and pore-detection voltage 304 (e.g., the applied voltage transitions between nanoporation magnitude 312 and pore-detection magnitude 314), the scope of the invention, including the use of buffer 306, equally includes embodiments in which there are temporal gaps between the applications of the nanoporation voltage and the applications of the pore-detection voltage, such as embodiments in which there is no applied voltage during the temporal gaps.

It is to be noted that, although FIG. 13 shows buffer period being used at transitions between nanoporation voltage 302 and pore-detection voltage 304 (e.g., the applied voltage transitions between nanoporation magnitude 312 and pore-detection magnitude 314), the scope of the invention includes the use of buffer 308 at other changes in voltage. There is therefore provided, in accordance with some applications of the invention apparatus comprising:

a dock;

a first dock-terminal positioned at the dock and a second dock-terminal positioned at the dock; and circuitry, configured to:

perform a subroutine in which the circuitry automatically:

applies a voltage between the first and second dock-terminals, periodically changes the magnitude of the voltage, and monitors conduction of a current between the first and second dock-terminals, and automatically stop the subroutine in response to detecting that an amplitude of the current exceeds a threshold amplitude, wherein the circuitry is provided to apply a buffer period after changing the magnitude of the voltage, and to ignore the current during the buffer period, such that the circuitry does not automatically stop the subroutine in response to the amplitude exceeding the threshold amplitude during the buffer period.

For some applications, rather than using buffer periods to avoid detection of current during capacitive current spikes, device 30 is configured to reduce the magnitude of induced capacitive current by making the changes in voltage more gradually. For example, increases and/or decreases between voltages 312 and 314 may be performed as smooth or stepwise gradual changes.

Alternatively, or in addition, to the use of buffer periods as described hereinabove, device 30 (e.g., circuitry 34 thereof) may be configured to use similar or different buffer periods in order to "ignore" any spike in current. For example, it has been observed by the inventors that instantaneously upon formation of a nanopore, a spike in current occurs. However, at that time the nanopore may not yet have a desired size (e.g., a desired width d6), but the current spike may nonetheless have a transient amplitude that is greater than threshold amplitude Therefore, for some applications, device 30 (e.g., circuitry 34) is configured to ignore the amplitude of the detected current during such a spike, in order to not interpret that spike as being indicative of a nanopore of the desired size.

Reference is again made to FIGS. 1-14. The nanoporation voltage described hereinabove may be considered to be a type of nanoporation energy. That is, electrical energy is used to ablate the nanopore in membrane 100. For some applications, the ablation of a nanopore in membrane 100 is achieved via application of a nanoporation energy other than electrical energy, mutatis mutandis. For example, electromagnetic radiation energy (e.g., light energy), and/or acoustic energy (e.g., ultrasound energy) may be used. Similarly, for some applications, chemical ablation is used. In each case, membrane 100 is configured to be susceptible to the particular form of ablation (e.g., the particular nanoporation energy) to be used. Typically, device 30 is configured to apply the nanoporation energy.

For applications in which the nanoporation energy is electromagnetic radiation energy, device 30 may comprise an electromagnetic radiation source. For some such applications, cartridge 60 comprises an optical fiber positioned and configured to direct the electromagnetic radiation from the source to membrane 100. For applications in which the nanoporation energy is acoustic energy, device 30 may comprise an acoustic energy source. For applications in which chemical ablation is used, device 30 may introduce the chemical-ablation agent.

For some applications the nanoporation voltage makes it difficult to monitor nanoporation (e.g., to monitor conduction of the pore-detection current), and therefore for some such applications it is advantageous to alternate between application of the nanoporation voltage and the pore-detection voltage, e.g., as described hereinabove. For some applications, the use of a nanoporation energy other than electrical energy advantageously facilitates pore-detection (i.e., application of the pore-detection voltage and monitoring of conduction of the pore-detection current) being performed continuously throughout the nanoporation subroutine—i.e., continuously while the nanoporation energy is being applied.

For some applications in which the nanoporation energy is a nanoporation energy other than electrical energy, a protective film analogous to film 120 is used, mutatis mutandis. For such applications, the protective film is configured to insulate the membrane from the nanoporation energy except for at the aperture, thereby biasing formation of the nanopore to the target region.

For some applications, the protective film (e.g., film 120) is removed after nanoporation (e.g., nanoporation subroutine 206) has been performed, and before the assay subroutine (e.g., assay subroutine 214) has been performed. For example, heat and/or a chemical agent may be applied (e g., by device 30, such as using heater 42) in order to degrade the film.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a sample suspected of containing an analyte, the apparatus comprising:
a test cartridge, comprising:
a casing that defines an internal space;
a membrane having a thickness of 0.1 nm-1 micron, the membrane disposed inside the casing, separating the internal space into a sample chamber and a second chamber, and fluidically and electrically isolating the second chamber from the sample chamber, and the casing shaped to define a port via which the sample is introducible into the sample chamber,
a first electrode, disposed within the sample chamber;
a first cartridge-terminal, electrically connected to the first electrode, and accessible from outside of the cartridge;
a second electrode, disposed within the second chamber;
a second cartridge-terminal, electrically connected to the second electrode, and accessible from outside of the cartridge; and
a device for use with the test cartridge, the device comprising:
a dock, comprising a first dock-terminal and a second dock-terminal, and configured to receive the cartridge such that docking of the cartridge with the dock places the first and second cartridge-terminals in electrical contact with the first and second dock-terminals; and
circuitry, electrically connected to the cartridge-terminals,
wherein the circuitry is configured to perform, while the cartridge remains docked with the dock:
(a) a verification step during which the circuitry verifies an absence of nanopores in the membrane by applying a pore-detection voltage between the first and second electrodes, and monitoring conduction, between the first and second electrodes, of a pore-detection current resulting from the applying of the pore-detection voltage,
(b) subsequently, a nanoporation subroutine, in which the circuitry:

(i) applies nanoporation energy to the membrane, the nanoporation energy configured to ablate a nanopore in the membrane, and
(ii) monitors conduction of the pore-detection current between the first and second electrodes, and
(iii) ends the nanoporation subroutine upon detecting that the pore-detection current exceeds a threshold amplitude, the threshold amplitude being indicative of successful formation of a nanopore, and
(c) subsequently, an assay subroutine, in which the circuitry:
(i) applies an assay voltage between the first and second electrodes, the assay voltage having a magnitude of 0.01-5 V, and
(ii) while driving the assay voltage, simultaneously monitors electrical conduction between at least two of the dock-terminals, and
wherein the circuitry is configured to enable the nanoporation subroutine only if the verification step (1) is performed between (i) docking of the cartridge with the dock, and (ii) performing the nanoporation subroutine, and (2) successfully verifies the absence of nanopores.

2. The apparatus according to claim 1, wherein the circuitry is configured:
to detect undocking of the cartridge from the dock, and
if the cartridge (i) becomes undocked from the dock after the absence of nanopores has been successfully verified, and (ii) is subsequently re-docked with the dock, to enable the nanoporation subroutine only if (1) the verification step is re-performed between (i) the re-docking and (ii) performing the nanoporation subroutine and the assay subroutine, and (2) the re-performed verification step successfully verifies the absence of nanopores.

3. The apparatus according to claim 1, wherein the cartridge comprises a positive-control moiety having a known concentration, disposed in the internal space, the positive-control moiety being a positive control for the analyte.

4. The apparatus according to claim 1, wherein the circuitry is configured such that steps (i) and (ii) of the nanoporation subroutine are performed iteratively.

5. The apparatus according to claim 1, wherein the circuitry is configured such that steps (i) and (ii) of the nanoporation subroutine are performed simultaneously.

6. The apparatus according to claim 1, wherein the circuitry is configured to apply the pore-detection voltage between the first and second electrodes during the nanoporation subroutine, the pore-detection current monitored during the nanoporation subroutine resulting from the applying of the pore-detection voltage.

7. The apparatus according to claim 1, further comprising a user interface, wherein the circuitry is configured to determine a concentration of the analyte in the sample by analyzing data indicative of the electrical conduction monitored during the assay subroutine, and to responsively drive the user interface to display information indicative of the concentration of the analyte.

8. The apparatus according to claim 1, wherein the circuitry is further configured to perform, while the cartridge remains docked with the dock, a positive-control subroutine in which the circuitry:
(i) applies the assay voltage between the first and second electrodes, and
(ii) while driving the assay voltage, simultaneously monitors electrical conduction between at least two of the dock-terminals.

9. The apparatus according to claim 8, wherein the cartridge comprises a positive-control moiety having a known concentration, disposed in the internal space, the positive-control moiety being a positive control for the analyte.

10. The apparatus according to claim 8, wherein the circuitry is configured to determine a concentration of the analyte in the sample by analyzing (i) data indicative of the electrical conduction monitored during the assay subroutine, and (ii) data indicative of the electrical conduction monitored during the positive-control subroutine.

11. The apparatus according to claim 1, wherein the nanoporation energy is a nanoporation voltage, the circuitry being configured to apply the nanoporation voltage between the first and second electrodes.

12. The apparatus according to claim 1, wherein the cartridge further comprises a protective film coating a surface of the membrane, the film shaped to define an aperture through the film such that a target region of the surface is exposed through the aperture, the protective film configured to insulate the membrane from the nanoporation energy except for at the aperture, thereby biasing formation of the nanopore to the target region.

13. The apparatus according to claim 12, wherein the film is an electrically-insulating film.

14. The apparatus according to claim 12, wherein a sample-side of the membrane faces the sample chamber, and a second-side of the membrane faces the second chamber, and wherein the film is disposed on the sample-side of the membrane.

15. The apparatus according to claim 12, wherein a sample-side of the membrane faces the sample chamber, and a second-side of the membrane faces the second chamber, and wherein the film is disposed on the second-side of the membrane.

16. The apparatus according to claim 12, wherein the cartridge further comprises a support on which the membrane is disposed, the support supporting the membrane and being shaped to define a window through which a zone of the membrane is exposed.

17. The apparatus according to claim 16, wherein a width of the aperture is smaller than a width of the window.

18. The apparatus according to claim 16, wherein:
the surface is a first surface of the membrane on a first side of the membrane, and the film coats the first surface of the membrane such that the target region is on the first surface of the membrane, and
the support is disposed against a second surface of the membrane on a second side of the membrane that is opposite the first side of the membrane, such that the zone of the membrane is on the second side of the membrane.

19. The apparatus according to claim 18, wherein the aperture and the window are positioned such that the target region is aligned with the zone.

20. The apparatus according to claim 16, wherein:
the surface is a first surface of the membrane on a first side of the membrane,
the support is disposed against the first side of the membrane, and
the film coats the first surface of the membrane within the zone, such that the target region is on the first surface of the membrane within the zone.

21. The apparatus according to claim 16, wherein the membrane is a silicon-based membrane, and the support comprises silicon.

22. The apparatus according to claim 12, wherein the membrane is a silicon-based membrane.

23. The apparatus according to claim 12, wherein the membrane is a 2D-material-based membrane.

24. The apparatus according to claim 12, wherein the aperture is exactly one aperture, and the film is shaped to define the exactly one aperture.

25. The apparatus according to claim 12, wherein chemistry of the surface at the target region is modified by a chemical moiety that is bound to the surface only at the target region.

\* \* \* \* \*